US012214182B2

(12) United States Patent
Polverelli et al.

(10) Patent No.: US 12,214,182 B2
(45) Date of Patent: *Feb. 4, 2025

(54) IMPLANTABLE PUMP SYSTEM HAVING AN UNDULATING MEMBRANE WITH IMPROVED HYDRAULIC PERFORMANCE

(71) Applicant: CorWave SA, Clichy (FR)

(72) Inventors: Luc Polverelli, Paris (FR); Leopold Maine, Asnieres-sur-Seine (FR); Carl N. Botterbusch, Wyomissing, PA (US); Silvere Lucquin, Paris (FR); Jean-Baptiste Drevet, Paris (FR); Adrien Guignabert, Meylan (FR); Patrick Meneroud, Vif (FR); Alexandra Schmidt, Paris (FR); Pier-Paolo Monticone, Geneva (CH)

(73) Assignee: CorWave SA, Clichy (FR)

( * ) Notice: Subject to any disclaimer, the term of this patent is extended or adjusted under 35 U.S.C. 154(b) by 167 days.

This patent is subject to a terminal disclaimer.

(21) Appl. No.: 17/930,404

(22) Filed: Sep. 7, 2022

(65) Prior Publication Data

US 2023/0001179 A1 Jan. 5, 2023

Related U.S. Application Data

(63) Continuation of application No. 16/766,267, filed as application No. PCT/IB2018/059199 on Nov. 22, (Continued)

(51) Int. Cl.
*A61M 5/142* (2006.01)
*A61M 60/122* (2021.01)
(Continued)

(52) U.S. Cl.
CPC ...... *A61M 60/148* (2021.01); *A61M 5/14224* (2013.01); *A61M 5/14276* (2013.01);
(Continued)

(58) Field of Classification Search
CPC .......... F04B 43/00; F04B 43/02; F04B 43/08; A61M 1/10; A61M 1/12; A61M 1/22
See application file for complete search history.

(56) References Cited

U.S. PATENT DOCUMENTS

| 2,842,067 | A | 7/1958 | John et al. |
| 3,107,630 | A | 10/1963 | Johnson et al. |

(Continued)

FOREIGN PATENT DOCUMENTS

| AU | 2013203301 A1 | 5/2013 |
| AU | 2013203301 B2 | 10/2015 |

(Continued)

OTHER PUBLICATIONS

Ando, et al., Electrocardiogram-Synchronized Rotational Speed Change Mode in Rotary Pumps Could Improve Pulsatility, Artificial Organs, 35(10):941-947 (2011).

(Continued)

*Primary Examiner* — Brian T Gedeon
(74) *Attorney, Agent, or Firm* — Greenberg Traurig, LLP; Christopher C. Bolten; Robert D. Ward

(57) ABSTRACT

An implantable pump system is provided, suitable for use as a left ventricular assist device (LVAD) system, having an implantable pump, a battery, a controller, and a programmer. The implantable pump includes a flexible membrane coupled to an actuator assembly via a skirt that extends toward the inlet of the pump and curves to guide blood toward the outlet. The actuator assembly is magnetically engageable with electromagnetic coils, so that when the electromagnetic coils are energized, the actuator assembly causes wavelike undulations to propagate along the flexible membrane to propel blood from the inlet, across the skirt, and through the outlet of the implantable pump. The controller may be programmed by a programmer to operate at frequencies and duty cycles that mimic physiologic flow (Continued)

rates and pulsatility while operating in an efficient manner that avoids thrombus formation, hemolysis and/or platelet activation.

24 Claims, 22 Drawing Sheets

Related U.S. Application Data 2018, now Pat. No. 11,446,480, which is a continuation of application No. 15/953,269, filed on Apr. 13, 2018, now Pat. No. 10,188,779.

(60) Provisional application No. 62/592,359, filed on Nov. 29, 2017.

(51) Int. Cl.
  *A61M 60/148* (2021.01)
  *A61M 60/178* (2021.01)
  *A61M 60/268* (2021.01)
  *A61M 60/40* (2021.01)
  *A61M 60/419* (2021.01)
  *A61M 60/427* (2021.01)
  *A61M 60/457* (2021.01)
  *A61M 60/459* (2021.01)
  *A61M 60/462* (2021.01)
  *A61M 60/508* (2021.01)
  *A61M 60/837* (2021.01)
  *A61M 60/857* (2021.01)
  *A61M 60/50* (2021.01)

(52) U.S. Cl.
  CPC ........ *A61M 60/122* (2021.01); *A61M 60/178* (2021.01); *A61M 60/268* (2021.01); *A61M 60/40* (2021.01); *A61M 60/419* (2021.01); *A61M 60/427* (2021.01); *A61M 60/457* (2021.01); *A61M 60/459* (2021.01); *A61M 60/462* (2021.01); *A61M 60/508* (2021.01); *A61M 60/837* (2021.01); *A61M 60/857* (2021.01); *A61M 60/50* (2021.01); *A61M 2205/18* (2013.01); *A61M 2205/3523* (2013.01); *A61M 2205/581* (2013.01); *A61M 2205/587* (2013.01); *A61M 2205/8206* (2013.01); *A61M 2209/088* (2013.01)

(56) References Cited

U.S. PATENT DOCUMENTS

| | | |
|---|---|---|
| 3,165,061 A | 1/1965 | Smith et al. |
| 3,608,088 A | 9/1971 | Dorman et al. |
| 3,620,651 A | 11/1971 | Peter |
| 3,743,446 A | 7/1973 | Mandroian |
| 3,765,175 A | 10/1973 | Ohnaka |
| 4,063,826 A | 12/1977 | Riepe |
| 4,277,706 A | 7/1981 | Isaacson |
| 4,384,830 A | 5/1983 | Wakelin |
| 4,484,095 A | 11/1984 | Neumann |
| 4,488,854 A | 12/1984 | Miller |
| 4,498,851 A | 2/1985 | Kolm et al. |
| 4,648,807 A | 3/1987 | Tippetts et al. |
| 4,753,221 A | 6/1988 | Kensey et al. |
| 4,906,229 A | 3/1990 | Wampler |
| 4,918,383 A | 4/1990 | Huff et al. |
| 4,931,036 A | 6/1990 | Kanai et al. |
| 4,939,405 A | 7/1990 | Okuyama et al. |
| 4,955,856 A | 9/1990 | Phillips |
| 4,995,857 A | 2/1991 | Arnold |
| 5,147,388 A | 9/1992 | Yamazaki |
| 5,263,978 A | 11/1993 | Kaufmann et al. |
| 5,275,580 A | 1/1994 | Yamazaki |
| 5,300,111 A | 4/1994 | Panton et al. |
| 5,360,445 A | 11/1994 | Goldowsky |
| 5,370,509 A | 12/1994 | Golding et al. |
| 5,525,041 A | 6/1996 | Deak |
| 5,588,812 A | 12/1996 | Taylor et al. |
| 5,840,070 A | 11/1998 | Wampler |
| 5,924,975 A | 7/1999 | Goldowsky |
| 5,982,801 A | 11/1999 | Deak |
| 6,030,336 A | 2/2000 | Franchi |
| 6,058,593 A | 5/2000 | Siess |
| 6,079,214 A | 6/2000 | Bishop |
| 6,083,260 A | 7/2000 | Aboul-Hosn |
| 6,116,862 A | 9/2000 | Rau et al. |
| 6,123,725 A | 9/2000 | Aboul-Hosn |
| 6,176,822 B1 | 1/2001 | Nix et al. |
| 6,176,848 B1 | 1/2001 | Rau et al. |
| 6,346,071 B1 | 2/2002 | Mussivand |
| 6,361,284 B2 | 3/2002 | Drevet |
| 6,395,026 B1 | 5/2002 | Aboul-Hosn et al. |
| 6,530,876 B1 | 3/2003 | Spence |
| 6,532,964 B2 | 3/2003 | Aboul-Hosn et al. |
| 6,658,740 B2 | 12/2003 | Habben |
| 6,659,740 B2 | 12/2003 | Drevet |
| 6,672,847 B2 | 1/2004 | Dooley |
| 6,723,039 B2 | 4/2004 | French et al. |
| 6,726,648 B2 | 4/2004 | Kaplon et al. |
| 6,732,501 B2 | 5/2004 | Yu et al. |
| 6,811,381 B2 | 11/2004 | Dooley |
| 6,848,001 B1 | 1/2005 | Sakamoto et al. |
| 6,935,344 B1 | 8/2005 | Aboul-Hosn et al. |
| 6,976,996 B1 | 12/2005 | Aboul-Hosn |
| 7,011,620 B1 | 3/2006 | Siess |
| 7,027,875 B2 | 4/2006 | Siess et al. |
| 7,182,727 B2 | 2/2007 | Aboul-Hosn |
| 7,323,961 B2 | 1/2008 | Drevet |
| 7,520,850 B2 | 4/2009 | Brockway |
| 7,696,634 B2 | 4/2010 | Filardo |
| 7,736,296 B2 | 6/2010 | Siess et al. |
| 7,839,007 B2 | 11/2010 | Filardo |
| 7,863,768 B2 | 1/2011 | Filardo |
| 7,889,877 B2 | 2/2011 | Lutz |
| 7,988,728 B2 | 8/2011 | Ayre |
| 8,012,079 B2 | 9/2011 | Delgado, III |
| 8,152,845 B2 | 4/2012 | Bourque |
| 8,157,720 B2 | 4/2012 | Marseille et al. |
| 8,167,593 B2 | 5/2012 | Gohean et al. |
| 8,333,686 B2 | 12/2012 | Marseille et al. |
| 8,343,029 B2 | 1/2013 | Farnan et al. |
| 8,366,401 B2 | 2/2013 | Pate et al. |
| 8,394,009 B2 | 3/2013 | Bolyard et al. |
| 8,394,010 B2 | 3/2013 | Farnan |
| 8,432,057 B2 | 4/2013 | Filardo |
| 8,449,444 B2 | 5/2013 | Poirier |
| 8,465,410 B2 | 6/2013 | Marseille et al. |
| 8,512,012 B2 | 8/2013 | Akdis et al. |
| 8,550,975 B2 | 10/2013 | Foster |
| 8,556,795 B2 | 10/2013 | Bolyard et al. |
| 8,562,508 B2 | 10/2013 | Dague et al. |
| 8,585,571 B2 | 11/2013 | Bachman et al. |
| 8,597,350 B2 | 12/2013 | Rudser et al. |
| 8,610,304 B2 | 12/2013 | Filardo |
| 8,714,944 B2 | 5/2014 | Drevet |
| 8,753,256 B2 | 6/2014 | Bolyard et al. |
| 8,784,291 B2 | 7/2014 | Farnan et al. |
| 8,821,366 B2 | 9/2014 | Farnan et al. |
| 8,821,527 B2 | 9/2014 | Farnan et al. |
| 8,827,888 B2 | 9/2014 | Bolyard et al. |
| 8,834,136 B2 | 9/2014 | Drevet |
| 8,852,072 B2 | 10/2014 | LaRose et al. |
| 8,870,739 B2 | 10/2014 | LaRose et al. |
| 8,956,275 B2 | 2/2015 | Bolyard et al. |
| 8,976,546 B2 | 3/2015 | Wang et al. |
| 9,022,916 B2 | 5/2015 | Farnan et al. |
| 9,080,564 B2 | 7/2015 | Drevet |
| 9,089,635 B2 | 7/2015 | Reichenbach et al. |
| 9,144,669 B2 | 9/2015 | Wieselthaler |
| 9,145,875 B2 | 9/2015 | Filardo |
| 9,173,984 B2 | 11/2015 | LaRose et al. |
| 9,211,367 B2 | 12/2015 | Farnan et al. |

(56) References Cited

U.S. PATENT DOCUMENTS

| | | |
|---|---|---|
| 9,308,304 B2 | 4/2016 | Peters et al. |
| 9,446,180 B2 | 9/2016 | Vadala, Jr. et al. |
| 9,526,819 B2 | 12/2016 | Chen |
| 9,572,915 B2 | 2/2017 | Heuring et al. |
| 9,579,437 B2 | 2/2017 | LaRose et al. |
| 9,616,158 B2 | 4/2017 | Yaghdjian |
| 9,694,123 B2 | 7/2017 | Bourque et al. |
| 9,731,057 B2 | 8/2017 | Garrigue |
| 9,744,279 B2 | 8/2017 | Tamez et al. |
| 9,786,150 B2 | 10/2017 | Kimball et al. |
| 9,861,728 B2 | 1/2018 | Farnan et al. |
| 9,956,333 B2 | 5/2018 | LaRose et al. |
| 9,968,720 B2 | 5/2018 | Botterbusch et al. |
| 10,166,319 B2 | 1/2019 | Botterbusch et al. |
| 10,188,779 B1 | 1/2019 | Polverelli et al. |
| 10,398,821 B2 | 9/2019 | Botterbusch et al. |
| 10,799,625 B2 | 10/2020 | Scheffler et al. |
| 10,933,181 B2 | 3/2021 | Le Duc De Lillers et al. |
| 11,097,091 B2 | 8/2021 | Botterbusch et al. |
| 11,191,946 B2 | 12/2021 | Snyder et al. |
| 11,298,522 B2 | 4/2022 | Botterbusch et al. |
| 11,446,480 B2 | 9/2022 | Polverelli et al. |
| 11,512,689 B2 | 11/2022 | Drevet et al. |
| 11,623,077 B2 | 4/2023 | Le Duc De Lillers et al. |
| 11,712,554 B2 | 8/2023 | Botterbusch et al. |
| 2001/0001278 A1 | 5/2001 | Drevet |
| 2002/0095210 A1 | 7/2002 | Finnegan et al. |
| 2002/0146333 A1 | 10/2002 | Drevet |
| 2002/0165426 A1 | 11/2002 | Sporer et al. |
| 2003/0002325 A1 | 1/2003 | Alvandpour et al. |
| 2004/0002624 A1 | 1/2004 | Yu et al. |
| 2004/0068220 A1 | 4/2004 | Couvillon et al. |
| 2005/0031474 A1 | 2/2005 | Zackl |
| 2005/0261543 A1 | 11/2005 | Abe et al. |
| 2005/0288543 A1 | 12/2005 | Stenberg et al. |
| 2006/0014999 A1 | 1/2006 | Heilman et al. |
| 2006/0155158 A1 | 7/2006 | Aboul-Hosn |
| 2006/0288543 A1 | 12/2006 | Lubera et al. |
| 2007/0299297 A1 | 12/2007 | Jarvik |
| 2008/0232987 A1 | 9/2008 | Drevet |
| 2009/0082778 A1 | 3/2009 | Beane et al. |
| 2010/0234941 A1 | 9/2010 | Finocchiaro et al. |
| 2010/0241223 A1 | 9/2010 | Lee et al. |
| 2010/0268333 A1 | 10/2010 | Gohean et al. |
| 2011/0124950 A1 | 5/2011 | Foster |
| 2011/0176945 A1 | 7/2011 | Drevet |
| 2011/0176946 A1 | 7/2011 | Drevet |
| 2011/0238172 A1 | 9/2011 | Akdis |
| 2011/0260449 A1 | 10/2011 | Pokorney |
| 2012/0089225 A1 | 4/2012 | Akkerman et al. |
| 2012/0177506 A1 | 7/2012 | Örter |
| 2012/0220816 A1 | 8/2012 | Peters et al. |
| 2012/0226350 A1 | 9/2012 | Rudser et al. |
| 2012/0323318 A1 | 12/2012 | Yusuf et al. |
| 2013/0042753 A1 | 2/2013 | Becker et al. |
| 2013/0078122 A1 | 3/2013 | Drevet |
| 2013/0178694 A1 | 7/2013 | Jeffery et al. |
| 2013/0267779 A1 | 10/2013 | Woolford et al. |
| 2013/0314047 A1 | 11/2013 | Eagle et al. |
| 2014/0023533 A1 | 1/2014 | Ishii et al. |
| 2014/0067057 A1 | 3/2014 | Callaway et al. |
| 2014/0187852 A1 | 7/2014 | Peters et al. |
| 2014/0207232 A1 | 7/2014 | Garrigue |
| 2014/0275723 A1 | 9/2014 | Fritz, IV et al. |
| 2014/0277423 A1 | 9/2014 | Alkhatib et al. |
| 2014/0303426 A1 | 10/2014 | Kerkhoffs et al. |
| 2014/0316426 A1 | 10/2014 | Gollner et al. |
| 2015/0167659 A1 | 6/2015 | Sauer |
| 2015/0273124 A1 | 10/2015 | Callaway et al. |
| 2015/0330383 A1 | 11/2015 | Letailleur et al. |
| 2016/0038664 A1 | 2/2016 | Callaway et al. |
| 2016/0051738 A1 | 2/2016 | Callaway et al. |
| 2016/0235899 A1 | 8/2016 | Yu et al. |
| 2016/0243294 A1 | 8/2016 | Peters et al. |
| 2017/0000934 A1 | 1/2017 | Miyakoshi |
| 2017/0012491 A1 | 1/2017 | Schob et al. |
| 2017/0266358 A1 | 9/2017 | Aber |
| 2017/0290966 A1 | 10/2017 | Botterbusch et al. |
| 2017/0290967 A1 | 10/2017 | Botterbusch et al. |
| 2017/0296723 A1 | 10/2017 | Garrigue |
| 2018/0038364 A1 | 2/2018 | Dumas et al. |
| 2018/0050143 A1 | 2/2018 | Nguyen et al. |
| 2018/0256798 A1 | 9/2018 | Botterbusch et al. |
| 2018/0369469 A1 | 12/2018 | Le Duc De Lillers et al. |
| 2019/0125949 A1 | 5/2019 | Botterbusch et al. |
| 2019/0268332 A1 | 8/2019 | Wang |
| 2019/0381227 A1 | 12/2019 | Botterbusch et al. |
| 2020/0368417 A1 | 11/2020 | Polverelli et al. |
| 2021/0085845 A1 | 3/2021 | West |
| 2021/0170160 A1 | 6/2021 | Le Duc De Lillers et al. |
| 2021/0172429 A1 | 6/2021 | Drevet et al. |
| 2021/0275797 A1 | 9/2021 | Snyder et al. |
| 2021/0379353 A1 | 12/2021 | Botterbusch et al. |
| 2022/0016412 A1 | 1/2022 | Bourquin et al. |

FOREIGN PATENT DOCUMENTS

| | | |
|---|---|---|
| CA | 2712945 A1 | 7/2009 |
| CN | 1257006 A | 6/2000 |
| CN | 1355715 A | 6/2002 |
| CN | 1714759 A | 1/2006 |
| CN | 101472627 A | 7/2009 |
| CN | 101878049 A | 11/2010 |
| CN | 102112744 A | 6/2011 |
| CN | 102284092 A | 12/2011 |
| CN | 106421939 A | 2/2017 |
| CN | 106489026 A | 3/2017 |
| CN | 107635602 A | 1/2018 |
| CN | 114367029 A | 4/2022 |
| CN | 114470512 A | 5/2022 |
| EP | 0412856 A1 | 2/1991 |
| EP | 0415949 A1 | 3/1991 |
| EP | 0412856 B1 | 1/1994 |
| EP | 0445782 B1 | 8/1994 |
| EP | 0925081 B1 | 12/2003 |
| EP | 0961621 B1 | 7/2004 |
| EP | 1551500 A2 | 7/2005 |
| EP | 1233797 B1 | 7/2006 |
| EP | 1337288 B1 | 3/2008 |
| EP | 1981585 A2 | 10/2008 |
| EP | 1644639 B1 | 2/2009 |
| EP | 2152339 A1 | 2/2010 |
| EP | 2249746 A1 | 11/2010 |
| EP | 2310067 A1 | 4/2011 |
| EP | 2600918 A1 | 6/2013 |
| EP | 2517739 B1 | 12/2013 |
| EP | 2704761 A1 | 3/2014 |
| EP | 2310067 B1 | 4/2014 |
| EP | 2753389 A1 | 7/2014 |
| EP | 2152339 B1 | 5/2015 |
| EP | 2891502 A1 | 7/2015 |
| EP | 2704761 B1 | 9/2015 |
| EP | 2736552 B1 | 9/2015 |
| EP | 2891502 B1 | 7/2016 |
| EP | 2164542 B1 | 8/2016 |
| EP | 2856190 B1 | 9/2016 |
| EP | 3141269 A1 | 3/2017 |
| EP | 3145558 A2 | 3/2017 |
| ES | 2587072 A1 | 10/2016 |
| FR | 355700 A | 11/1905 |
| FR | 2650862 B1 | 11/1991 |
| FR | 2744769 A1 | 8/1997 |
| FR | 2744769 B1 | 2/1999 |
| FR | 2861910 B1 | 1/2006 |
| FR | 2905147 A1 | 2/2008 |
| FR | 3032917 A1 | 8/2016 |
| GB | 662047 A | 11/1951 |
| JP | 2011509801 A | 3/2011 |
| KR | 20130068373 A | 6/2013 |
| WO | WO-8910763 A1 | 11/1989 |
| WO | WO-9008260 A1 | 7/1990 |
| WO | WO-9729282 A1 | 8/1997 |
| WO | WO-9959652 A1 | 11/1999 |
| WO | WO-0037126 A1 | 6/2000 |

(56) References Cited

FOREIGN PATENT DOCUMENTS

| WO | WO-0074747 A1 | 12/2000 |
|---|---|---|
| WO | WO-2007053881 A1 | 5/2007 |
| WO | WO-2011056823 A2 | 5/2011 |
| WO | WO-2016179262 A1 | 11/2016 |
| WO | WO-2017087717 A1 | 5/2017 |
| WO | WO-2017087785 A1 | 5/2017 |
| WO | WO-2019019206 A1 | 1/2019 |
| WO | WO-2019092175 A1 | 5/2019 |
| WO | WO-2019154804 A1 | 8/2019 |
| WO | WO-2020115607 A2 | 6/2020 |

OTHER PUBLICATIONS

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Extended European Search Report dated Aug. 25, 2021 in EP Patent Application Serial No. 21168340.4 (0231).

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl. No. PCT/IB2018/059199, 13 pages (0510).

International Search Report & Written Opinion dated May 14, 2021 in Int'l PCT Patent Appl. Serial No. PCT/IB2021/051879 (0910).

International Search Report & Written Opinion dated Jun. 28, 2017 in Int'l PCT Patent Application Serial No. PCT/IB2017/052068 (0210).

International Search Report & Written Opinion dated Jul. 15, 2020 in Int'l PCT Patent Appl. Serial No. PCT/IB2019/060144 (0610).

International Search Report & Written Opinion dated Aug. 22, 2017 in Int'l PCT Patent Application Serial No. PCT/IB2017/052069 (0310).

International Search Report and Written Opinion dated Apr. 16, 2019 in Int'l. PCT Patent Appl. Serial No. PCT/EP2018/080749 (English Translation of ISR only) (0810).

International Search Report and Written Opinion dated Jun. 25, 2020 in International PCT Patent Application Serial No. PCT/IB2020/052337 (0710 PCT).

International Search Report and Written Opinion dated Aug. 3, 2018 in Int'l PCT Patent Appl. Serial No. PCT/IB2018/052215 (0410).

Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).

Islam et al., Left Ventricular Assist Devices and Gastrointestinal Bleeding: A Narrative Review of Case Reports and Case Series, Clinical Cardiology, 36(4):190-200 (2013).

Jorde, et al., Identification and Management of Pump Thrombus in the HeartWare Left Ventricular Assist Device System, JACC: Heart Failure, 3(11):849-856 (2015).

Latham, et al., Parameter Estimation and a Series of Nonlinear Observers for the System Dynamics of a Linear Vapor Compressor, IEEE Transactions on Industrial Electronics, 63(11):6736-6744 (2016).

Leverett, et al., Red Blood Cell Damage by Shear Stress, Biophysical Journal, 12(3):257-273 (1972).

Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).

Mancini, et al., Left Ventricular Assist Devices, A Rapidly Evolving Alternative to Transplant, Journal of the American College of Cardiology, 653:2542-2555 (2015).

Mboup, et al., Numerical Differentiation With Annihilators in Noisy Environment, Numerical Algorithms, 50(4):439-467 (2009).

Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).

Mercorelli, P., A Motion-Sensorless Control for Intake Valves in Combustion Engines, IEEE Transactions on Industrial Electronics, 64(4):3402-3412 (2017).

Mercorelli, P., An Adaptive and Optimized Switching Observer for Sensorless Control of an Electromagnetic Valve Actuator in Camless Internal Combustion Engines, Asian Journal of Control, 16(4):959-973 (2014).

Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).

Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).

Pagani, Francis D., MD, Phd, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.

Perschall, et al., The Progressive Wave Pump: Numerical Multiphysics Investigation of a Novel Pump Concept With Potential to Ventricular Assist Device Application, Artificial Organs, 35(9):E179-E190 (2012).

Rahman, et al., Position Estimation in Solenoid Actuators, IEEE Transactions on Industry Applications, 32(3):552-559 (1996).

Rigatos, G., Differential Flatness Theory ad Flatness-Based Control, in Nonlinear Control and Filtering Using Differential Flatness Approaches, 25(2):47-101 (2015).

Wang, et al., Rotary Blood Pump Control Strategy for Preventing Left Ventricular Suction, ASAIO Journal, 61(1):21-30(2015).

Wang., Quadrotor Analysis and Model Free Control with Comparisons, Universite Paris Sud—Paris XI, (2013).

Weidemann, Daniel., Thesis entitled, Permanent Magnet Reluctance Actuators for Vibration Testing, Completed at the Institute of Applied Mechanics, Technische Universitat Munchen, Apr. 2013.

Yuan, et al., The Spectrum of Complications Following Left Ventricular Assist Device Placement, Journal of Cardiac Surgery, 27:630-638 (2012).

Zhang, et al., Study on Self-Sensor of Linear Moving Magnet Compressor's Piston Stroke, IEEE Sensors Journal, 9(2):154-158 (2009).

U.S. Appl. No. 15/484,101 / U.S. Pat. No. 9,968,720, filed Apr. 10, 2017 / May 15, 2018.

(56) References Cited

OTHER PUBLICATIONS

U.S. Appl. No. 15/484,108 / U.S. Pat. No. 10,166,319, filed Apr. 10, 2017 / Jan. 1, 2019.
U.S. Appl. No. 15/940,856 / U.S. Pat. No. 10,933,181, filed Mar. 29, 2018 / Mar. 2, 2021.
U.S. Appl. No. 15/953,269 / U.S. Pat. No. 10,188,779, filed Apr. 13, 2018 / Jan. 29, 2019.
U.S. Appl. No. 15/976,831 / U.S. Pat. No. 10,398,821, filed May 10, 2018 / Sep. 3, 2019.
U.S. Appl. No. 16/234,519 / U.S. Pat. No. 11,097,091, filed Dec. 27, 2018 / Aug. 24, 2021.
U.S. Appl. No. 16/557,711 / U.S. Pat. No. 11,298,522, filed Aug. 30, 2019 / Aug. 30, 2019.
U.S. Appl. No. 16/762,909, filed May 8, 2019.
U.S. Appl. No. 16/766,267 / U.S. Pat. No. 11,446,480, filed May 21, 2020 / Sep. 20, 2022.
U.S. Appl. No. 16/819,021 / U.S. Pat. No. 10,799,625, filed Mar. 13, 2020 / Oct. 31, 2020.
U.S. Appl. No. 17/179,961, filed Feb. 19, 2021.
U.S. Appl. No. 17/193,867 / U.S. Pat. No. 11,191,946, filed Mar. 5, 2021 / Dec. 7, 2021.
U.S. Appl. No. 17/299,749, filed Jun. 3, 2021.
U.S. Appl. No. 17/409,100, filed Aug. 23, 2021.
U.S. Appl. No. 17/474,935, filed Sep. 14, 2021.
U.S. Appl. No. 17/658,074, filed Apr. 5, 2022.
International Search Report & Written Opinion dated Apr. 2, 2024 in Int'l PCT Patent Appl. Serial No. PCT/IB2023/061509 (131001).
International Search Report & Written Opinion dated Oct. 9, 2023 in Int'l PCT Patent Appl. Serial No. PCT/IB2023/054203 (111001).

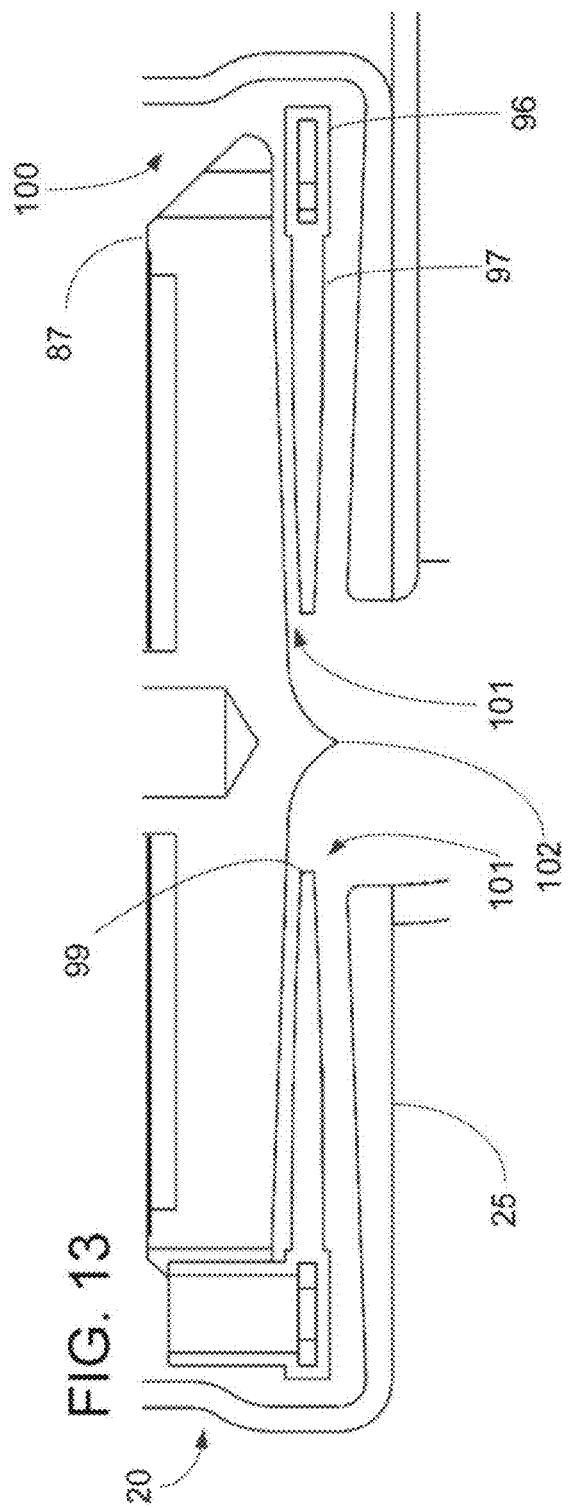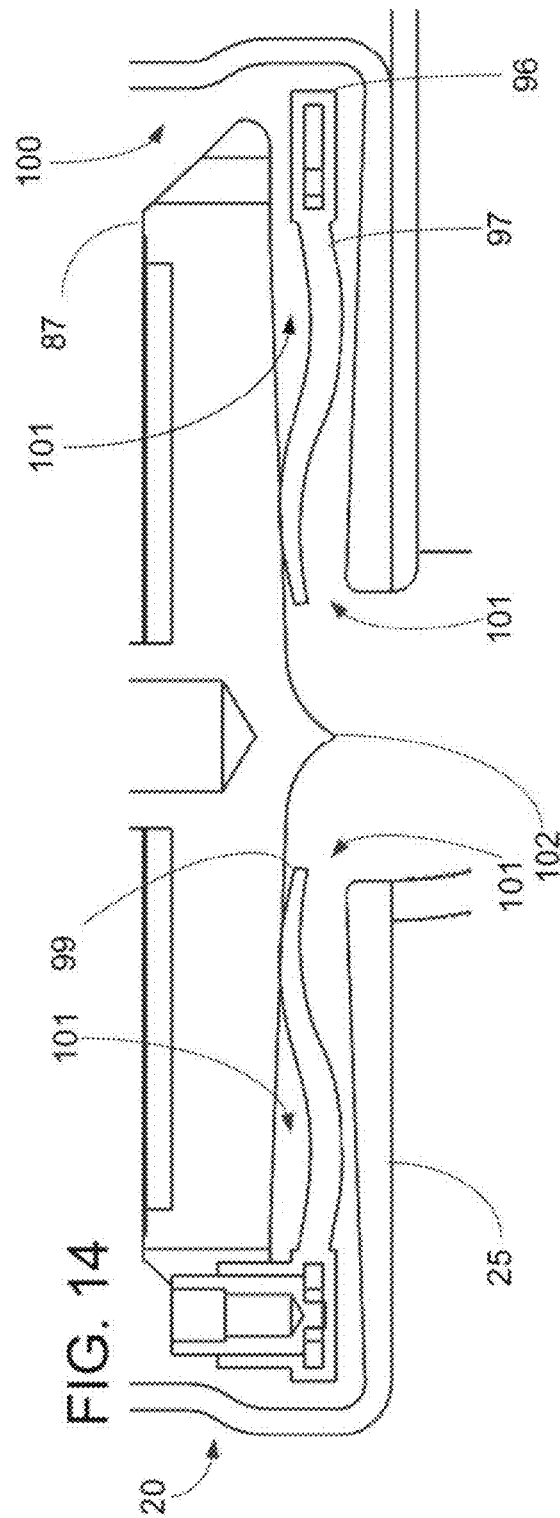

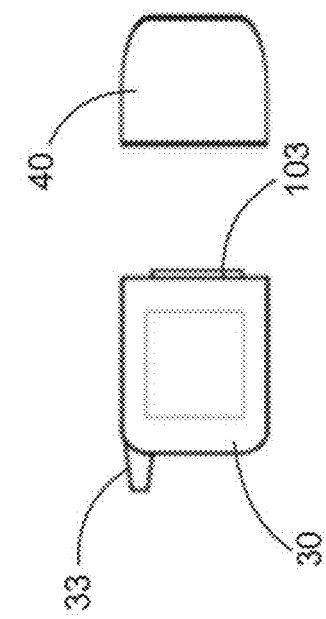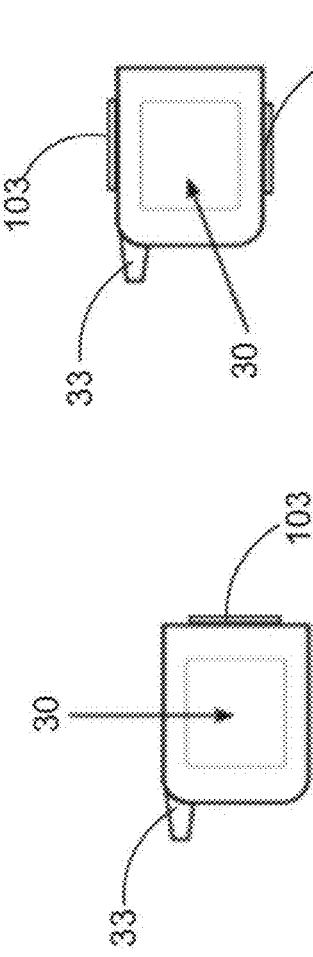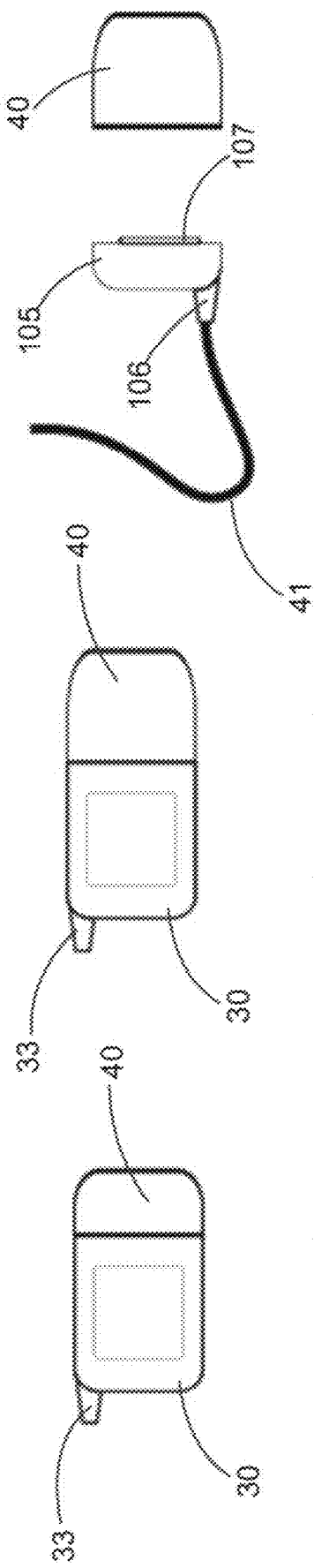

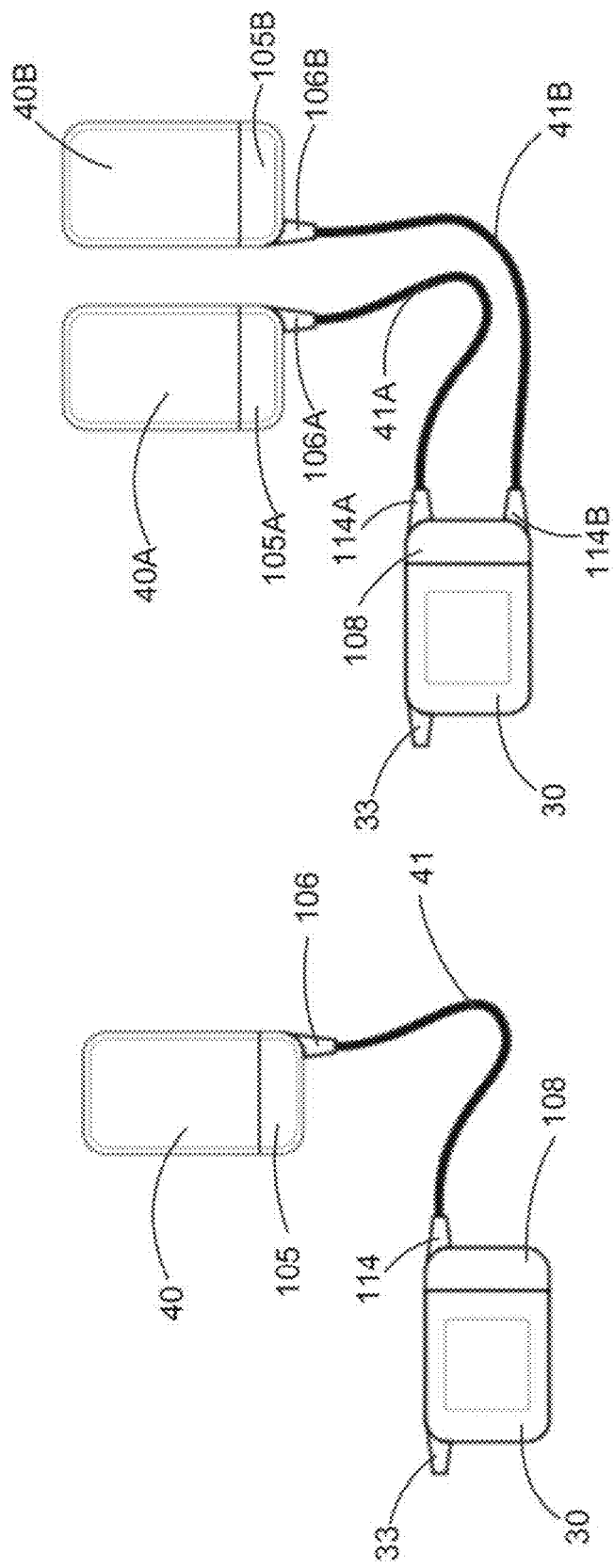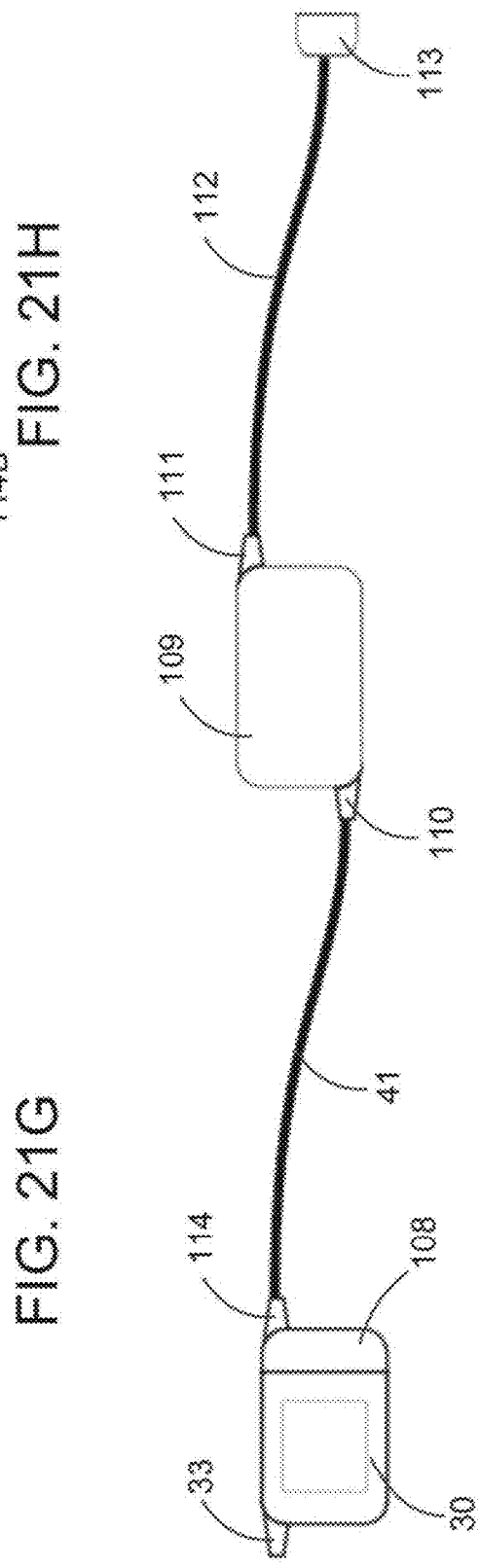

IMPLANTABLE PUMP SYSTEM HAVING AN UNDULATING MEMBRANE WITH IMPROVED HYDRAULIC PERFORMANCE

CROSS-REFERENCE TO RELATED APPLICATION

This application is a continuation of U.S. patent application Ser. No. 16/766,267, filed May 21, 2020, now U.S. Pat. No. 11,446,480, which is a national phase application under 35 U.S.C. § 371 of International PCT Patent Application Serial No. PCT/IB2018/059199, filed Nov. 22, 2018, which claims priority to U.S. patent application Ser. No. 15/953,269, filed Apr. 13, 2018, now U.S. Pat. No. 10,188,779 and U.S. Provisional Patent Application Ser. No. 62/592,359, filed Nov. 29, 2017, the entire contents of each of which are incorporated herein by reference.

FIELD OF THE INVENTION

The present invention relates generally to heart pumps and more particularly to implantable pumps having an undulating membrane with improved hydraulic performance designed to reduce hemolysis and platelet activation.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to pump oxygenated blood throughout the body.

The Centers for Disease Control and Prevention (CDC) estimate that about 5.1 million people in the United States suffer from some form of heart failure. Heart failure is generally categorized into four different stages with the most severe being end stage heart failure. End stage heart failure may be diagnosed where a patient has heart failure symptoms at rest in spite of medical treatment. Patients at this stage may have systolic heart failure, characterized by decreasing ejection fraction. In patients with systolic heart failure, the walls of the ventricle, which are typically thick in a healthy patient, become thin and weak. Consequently, during systole a reduced volume of oxygenated blood is ejected into circulation, a situation that continues in a downward spiral until death. A patient diagnosed with end stage heart failure has a one-year mortality rate of approximately 50%.

For patients that have reached end stage heart failure, treatment options are limited. In addition to continued use of drug therapy commonly prescribed during earlier stages of heart failure, the typical recommend is cardiac transplantation and implantation of a mechanical assist device. While a cardiac transplant may significantly prolong the patient's life beyond the one year mortality rate, patients frequently expire while on a waitlist for months and sometimes years awaiting a suitable donor heart. Presently, the only alternative to a cardiac transplant is a mechanical implant. While in recent years mechanical implants have improved in design, typically such implants will prolong a patient's life by a few years at most, and include a number of co-morbidities.

One type of mechanical implant often used for patients with end stage heart failure is a left ventricular assist device (LVAD). The LVAD is a surgically implanted pump that draws oxygenated blood from the left ventricle and pumps it directly to the aorta, thereby off-loading (reducing) the pumping work of the left ventricle. LVADs typically are used either as "bridge-to-transplant therapy" or "destination therapy." When used for bridge-to-transplant therapy, the LVAD is used to prolong the life of a patient who is waiting for a heart transplant. When a patient is not suitable for a heart transplant, the LVAD may be used as a destination therapy to prolong the life, or improve the quality of life, of the patient, but generally such prolongation is for only a couple years.

Generally, a LVAD includes an inlet cannula, a pump, and an outlet cannula, and is coupled to an extracorporeal battery and control unit. The inlet cannula typically directly connected to the left ventricle, e.g., at the apex, and delivers blood from the left ventricle to the pump. The outlet cannula typically connected to the aorta distal to the aortic valve, delivers blood from the pump to the aorta. Typically, the outlet cannula of the pump is extended using a hose-type structure, such as a Dacron graft, to reach a proper delivery location on the aorta. Early LVAD designs were of the reciprocating type but more recently rotary and centrifugal pumps have been used.

U.S. Pat. No. 4,277,706 to Isaacson, entitled "Actuator for Heart Pump," describes a LVAD having a reciprocating pump. The pump described in the Isaacson patent includes a housing having an inlet and an outlet, a cavity in the interior of the pump connected to the inlet and the outlet, a flexible diaphragm that extends across the cavity, a plate secured to the diaphragm, and a ball screw that is configured to be reciprocated to drive the plate and connected diaphragm from one end of the cavity to the other end to simulate systole and diastole. The ball screw is actuated by a direct current motor. The Isaacson patent also describes a controller configured to manage the revolutions of the ball screw to control the starting, stopping and reversal of directions to control blood flow in and out of the pump.

Previously-known reciprocating pump LVADs have a number of drawbacks. Such pumps often are bulky, heavy and may require removal of bones and tissue in the chest for implantation. They also require a significant amount of energy to displace the blood by compressing the cavity. Moreover, the pump subjects the blood to significant pressure fluctuations as it passes through the pump, resulting in high shear forces and risk of hemolysis. These pressure fluctuations may be exaggerated at higher blood flow rates. Further, depending on the geometry of the pump, areas of little or no flow may result in flow stagnation, which can lead to thrombus formation and potentially fatal medical conditions, such as stroke. Finally, the positive displacement pumps like the one described in the Isaacson patent are incapable of achieving pulsatility similar to that of the natural heart, e.g., roughly 60 to 100 beats per minute, while maintaining physiological pressure gradients.

LVADs utilizing rotary and centrifugal configurations also are known. For example, U.S. Pat. No. 3,608,088 to Reich, entitled "Implantable Blood Pump," describes a centrifugal pump to assist a failing heart. The Reich patent describes a centrifugal pump having an inlet connected to a rigid cannula that is coupled to the left ventricular cavity and a Dacron graft extending from the pump diffuser to the aorta.

A pump includes an impeller that is rotated at high speeds to accelerate blood, and simulated pulsations of the natural heart by changing rotation speeds or introducing a fluid oscillator.

U.S. Pat. No. 5,370,509 to Golding, entitled "Sealless Rotodynamic Pump with Fluid Bearing," describes an axial blood pump capable for use as a heart pump. One embodiment described involves an axial flow blood pump with impeller blades that are aligned with the axes of the blood inlet and blood outlet. U.S. Pat. No. 5,588,812 to Taylor, entitled "Implantable Electrical Axial-Flow Blood Pump," describes an axial flow blood pump similar to that of the Golding patent. The pump described in the Taylor patent has a pump housing that defines a cylindrical blood conduit through which blood is pumped from the inlet to the outlet, and rotor blades that rotate along the axis of the pump to accelerate blood flowing through the blood conduit.

While previously-known LVAD devices have improved, those pump designs are not without problems. Like reciprocating pumps, rotary and centrifugal pumps are often bulky and difficult to implant. Rotary pumps, while mechanically different from positive displacement pumps, also exhibit undesirable characteristics. Like positive displacement pumps, rotary pumps apply significant shear forces to the blood, thereby posing a risk of hemolysis and platelet activation. The very nature of a disk or blade rotating about an axis results in areas of high velocity and low velocity as well as vibration and heat generation. Specifically, the area near the edge of the disk or blade furthest from the axis of rotation experiences higher angular velocity and thus flow rate than the area closest to the axis of rotation. The resulting radial velocity profile along the rotating blade results in high shear forces being applied to the blood. In addition, stagnation or low flow rates near the axis of rotation may result in thrombus formation.

While centrifugal pumps may be capable generating pulsatile flow by varying the speed of rotation of the associated disk or blades, this only exacerbates the problems resulting from steep radial velocity profiles and high shear force. In common practice, the output of currently available rotary pumps, measured as flow rate against a given head pressure, is controlled by changing the rotational speed of the pump. Given the mass of the rotating member, the angular velocity of the rotating member, and the resulting inertia, a change in rotational speed cannot be instantaneous but instead must be gradual. Accordingly, while centrifugal pumps can mimic a pulsatile flow with gradual speed changes, the resulting pulse is not "on-demand" and does not resemble a typical physiological pulse.

Moreover, rotary pumps typically result in the application of non-physiologic pressures on the blood. Such high operating pressures have the unwanted effect of overextending blood vessels, which in the presence of continuous flow can cause the blood vessels to fibrose and become inelastic. This in turn can lead to loss of resilience in the circulatory system, promoting calcification and plaque formation. Further, if the rotational speed of a pump is varied to simulate pulsatile flow or increase flow rate, the rotary pump is less likely to be operated at its optimal operating point, reducing efficiency and increasing energy losses and heat generation.

LVADs may also be configured to increase blood flow to match the demand of the patient. Numerous publications and patents describe methods for adjusting LVAD pump flow to match that demanded by the patient. For example U.S. Pat. No. 7,520,850 to Brockway, entitled "Feedback control and ventricular assist devices," describes systems and methods for employing pressure feedback to control a ventricular assist device. The system described in the Brockway patent attempts to maintain a constant filling of the ventricle by measuring ventricular pressure and/or ventricular volume. While such systems can achieve flow rates as high as 8 or 9 liters per minute, these flow rates generally are outside of the efficient range of operation for current rotary pumps, which are typically tuned to operate in a range of 4 to 6 liters per minute. Thus, increasing the flow rate in rotary pumps to match patient demanded results in non-optimal pump performance.

Pumps other than of the rotary and positive displacement types are known in the art for displacing fluid. For example, U.S. Pat. Nos. 6,361,284 and 6,659,740, both to Drevet, entitled "Vibrating Membrane Fluid Circulator," describe pumps in which a deformable membrane is vibrated to propel fluid through a pump housing. In these patents, vibratory motion applied to the deformable membrane causes wave-like undulations in the membrane that propel the fluid along a channel. Different flow rates may be achieved by controlling the excitation applied to the membrane.

U.S. Pat. No. 7,323,961 to Drevet, entitled "Electromagnetic Machine with a Deformable Membrane," describes a device in which a membrane is coupled in tension along its outer edge to an electromagnetic device arranged to rotate around the membrane. As the electromagnetic device rotates, the outer edge of the membrane is deflected slightly in a direction normal to the plane of the membrane. These deflections induce a wave-like undulation in the membrane that may be used to move a fluid in contact with the membrane.

U.S. Pat. No. 9,080,564 to Drevet, entitled "Diaphragm Circulator," describes a tensioned deformable membrane in which undulations are created by electromechanically moving a magnetized ring, attached to an outer edge of a deformable membrane, over a coil. Axial displacement of magnetized ring causes undulations of membrane. Like in the '961 patent, the membrane undulations can be controlled by manipulating the magnetic attraction. U.S. Pat. No. 8,714,944 to Drevet, entitled "Diaphragm pump with a Crinkle Diaphragm of Improved Efficiency" and U.S. Pat. No. 8,834,136 to Drevet, entitled "Crinkle Diaphragm Pump" teach similar types of vibrating membrane pumps.

None of the foregoing patents to Drevet describe a vibratory membrane pump suitable for use in a biological setting, or capable of pumping blood over extended periods that present a low risk of flow stagnation leading to thrombus formation.

U.S. Patent Publication Nos. 2017/0290966 and 2017/0290967 to Botterbusch, the entire contents of each of which are incorporated herein by reference, describe implantable cardiovascular blood pumps having a flexible membrane coupled to an electromagnetic actuator assembly that causes wavelike undulations to propagate along the flexible membrane to propel blood through the pump while avoiding thrombus formation, hemolysis and/or platelet activation. The Botterbusch pumps generate hydraulic power—flow and pressure—by translating the linear motion of the electromagnetic actuator, to the flexible membrane, which deforms through its interaction with the blood, translating energy to the blood. The flexible membrane is oriented at a 90° angle to the motion of the linear actuator such that the outer edge of the membrane is the first element to engage the blood. As a result, there is a risk of energy loss at the inlet to the membrane, which affects the hydraulic power generation by the pump.

What is needed is an energy efficient implantable pump having light weight, small size, and fast start and stop response that can operate efficiently and with improved hydraulic performance and minimal blood damage over a wide range of flow rates.

SUMMARY OF THE INVENTION

The present invention overcomes the drawbacks of previously-known LVAD systems and methods by providing an implantable pump system having an undulating membrane capable of producing a wide range of physiological flow rates while applying low shear forces to the blood, thereby reducing hemolysis and platelet activation relative to previously-known systems.

In accordance with one aspect of the invention, the implantable blood pump system includes a housing having an inlet and an outlet for implantation at a patient's heart, a membrane disposed within the housing, a skirt disposed within the housing and coupled to the membrane, the skirt sized and shaped to extend toward the inlet and to curve toward the outlet, and an actuator disposed within the housing, wherein the actuator causes the membrane to reciprocate and deform in a wave-like manner. During operation of the pump system, blood enters the inlet, flows toward the skirt which guides the blood towards the membrane, and is propelled across the membrane to the outlet. For example, the skirt may have a J-shaped cross-section.

The bottom surface of the actuator and an interior portion of the housing adjacent the outlet may form a flow channel within which the membrane is suspended. In addition, the actuator and an interior surface of the housing adjacent the inlet may form a delivery channel extending from the inlet to the flow channel. Accordingly, the skirt may be disposed within the delivery channel such that during operation the skirt guides blood from the delivery channel to the flow channel while reducing recirculation of the blood. For example, during operation the skirt guides blood from the delivery channel to the flow channel such that blood is propelled evenly across the membrane.

In one embodiment, the implantable blood pump system further includes a rigid ring fixed concentrically around the actuator, wherein the rigid ring is disposed within the delivery channel such that during operation the rigid ring guides blood from the delivery channel across the skirt to the flow channel while reducing recirculation of the blood. In addition, the skirt may include a plurality of bellows between the rigid ring and the curved portion of the skirt. The plurality of bellows expand and contract such that during operation the rigid ring guides blood from the delivery channel across the plurality of bellows and the skirt to the flow channel while reducing recirculation of the blood.

The actuator may include an electromagnet assembly that selectively generates a magnetic field. The implantable blood pump system further may include a magnetic ring coupled to the skirt, such that the magnetic ring is concentrically suspended around the actuator and reciprocates responsive to the magnetic field. For example, the electromagnet assembly may include first and second electromagnetic coils such that the magnetic ring is caused to move when at least one of the first or second electromagnetic coils is energized.

The implantable blood pump system also may include one or more suspension rings concentrically disposed around and coupled to the actuator and the magnetic ring to permit the magnetic ring to reciprocate over the actuator, wherein the magnetic ring is coupled to each of the skirt and the one or more suspension rings by a plurality of posts. The one or more suspension rings exert a spring force on the magnetic ring when the magnetic ring reciprocates over the actuator. In addition, the implantable blood pump system may include a fixation ring concentrically coupled to the actuator, such that the fixation ring anchors the actuator within the housing.

In accordance with one aspect of the invention, the inlet of the housing is coupled to an inflow cannula, and the outlet of the housing is coupled to an outflow cannula, wherein the outflow cannula is disposed coaxially within the inflow cannula.

The implantable blood pump system also may include a rechargeable battery for energizing the implantable blood pump, and an extracorporeal controller operatively coupled in electrical communication with the actuator via a transcutaneous cable, the extracorporeal controller comprising a power connector that may be operatively coupled in electrical communication with the rechargeable battery. In addition, the implantable blood pump system may include an extension cable having a first end that is operatively coupled in electrical communication with the power connector of the extracorporeal controller, and a second end that is operatively coupled in electrical communication with the rechargeable battery. Accordingly, the power connector of the extracorporeal controller may be operatively coupled in electrical communication with the rechargeable battery remotely via the extension cable. The extracorporeal controller may be programmed to operate the actuator to cause the membrane to reciprocate and deform in a wave-like manner to propel blood from the inlet across the skirt to the outlet with a pulsatile flow. The implantable blood pump system also may include a programmer that communicates with the controller to set and change operating parameters of the actuator.

In accordance with another aspect of the invention, a blood pump for use in a patient is provided. The blood pump may include an implantable housing having an inlet, an outlet, and a longitudinal axis, the implantable housing defining a delivery channel parallel to the longitudinal axis and a flow channel perpendicular to the longitudinal axis, an actuator system disposed within the implantable housing comprising a stationary component and a moving component, the moving component concentrically suspended around the stationary component, a membrane disposed within the implantable housing, and a skirt coupled to the moving component and the membrane, the skirt sized and shaped to extend in the delivery channel toward the inlet and to curve into the flow channel toward the outlet. The actuator system selectively generates a magnetic field that causes the moving component to reciprocate at a predetermined frequency and amplitude relative to the stationary component, thereby causing blood flow to enter the implantable housing via the inlet, divide in the delivery channel around the skirt, and curve toward the flow channel across the membrane to the outlet. For example, the actuator system may include first and second electromagnetic coils such that the moving component, e.g., a magnetic ring, is caused to move when at least one of the first or second electromagnetic coils is energized.

BRIEF DESCRIPTION OF THE DRAWINGS

FIG. 13 is a cross-sectional view of a lower portion of the implantable pump depicting the flow channel and membrane assembly in a resting position.

FIG. 14 is a cross-sectional view of a lower portion of the implantable pump depicting the flow channel and membrane assembly with the membrane undulating.

FIG. 16A illustrates blood flow across a planar ring membrane support, whereas

FIGS. 21A-H illustrates various configurations for coupling a battery to a controller of the present invention, and FIG. 21I illustrates a controller coupled to a power supply.

DETAILED DESCRIPTION

The implantable pump system of the present invention is particularly well-suited for use as a left ventricular assist device (LVAD), and includes an undulating membrane pump suitable for long-term implantation in a patient having end term heart failure. An implantable pump system constructed in accordance with the principles of the present invention includes an implantable pump and an extracorporeal battery, controller and programmer. The implantable pump includes a housing having an inlet, and outlet, a flexible membrane, and an actuator assembly. When configured as an LVAD, the housing includes an inlet cannula that is inserted into a patient's left ventricle near the apex and an outlet cannula that is surgically placed in fluid communication with the patient's aorta. By activating the actuator assembly within the implantable pump, membrane is induced to undulate, thereby causing blood to be drawn into the pump through the inlet cannula and expelled through the outlet cannula into the aorta. Flow rate and pulsatility may be manipulated by changing one or more of the frequency, amplitude and duty cycle of the actuator assembly.

For improved hydraulic performance, the implantable pump may include a skirt disposed within the housing to guide blood flow from the inlet of the pump towards the outlet. The skirt may be positioned within the housing such that blood flows across opposing sides of the skirt and towards the undulating membrane upon activation of the pump.

Figure 1:
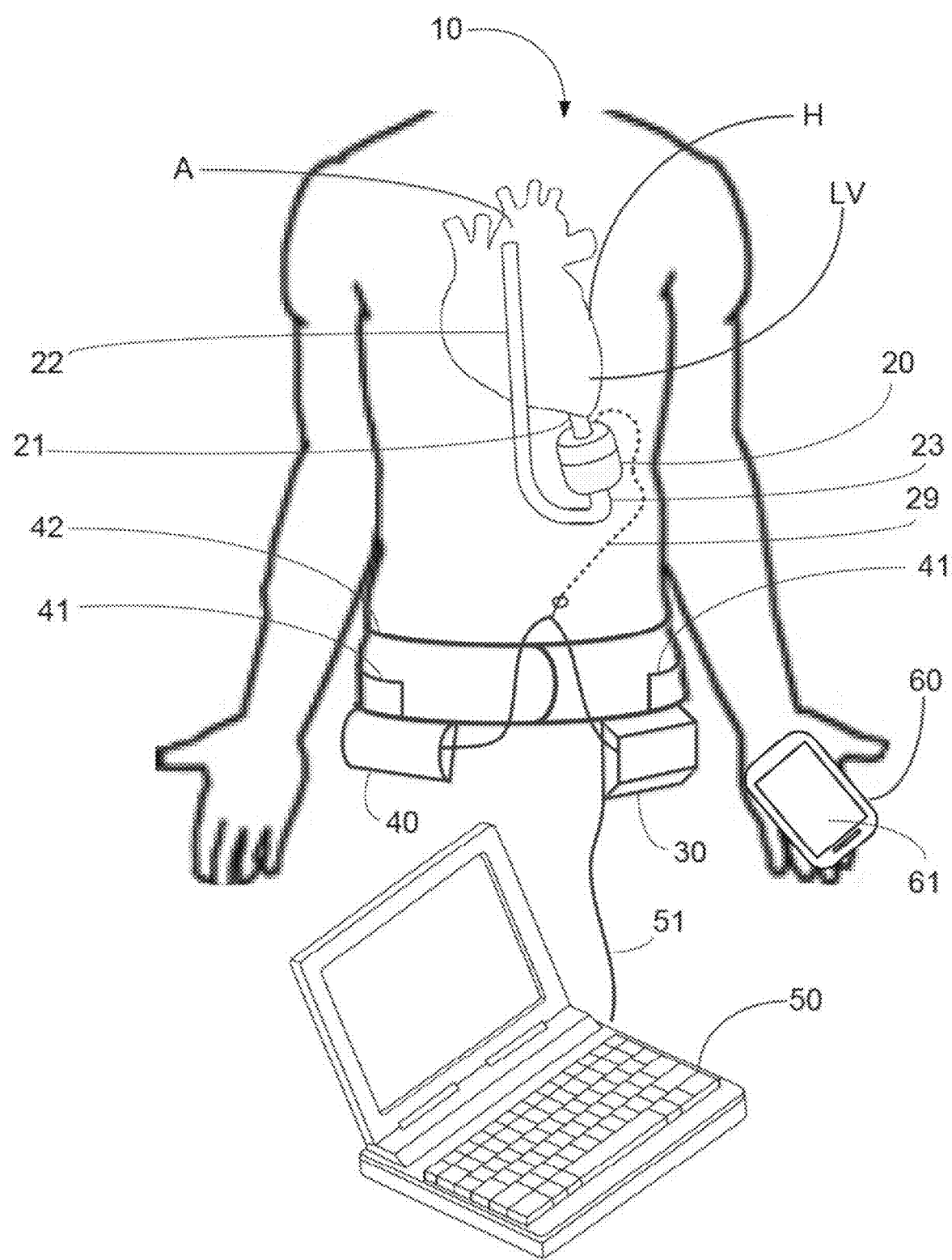
FIG. 1 depicts an exemplary embodiment of the pump system of the present invention comprising an implantable pump, controller, battery, programmer and mobile device.

Referring now to FIG. 1, pump system 10 constructed in accordance with the principles of the present invention is described. Pump system 10 includes implantable pump 20, controller 30, battery 40, programmer 50 and optionally, a software module programmed to run on mobile device 60. Implantable pump 20 is configured to be implanted within a patient's chest so that inlet cannula 21 is coupled to left ventricle LV of heart H. Outlet cannula 22 of pump 20 is configured to be coupled to aorta A. Inlet cannula 21 preferably is coupled to the apex of left ventricle LV, while outlet cannula 22 is coupled to aorta A in the vicinity of the ascending aorta, above the level of the cardiac arteries. Implantable pump 20 may be affixed within the patient's chest using a ring-suture or other conventional technique. Outlet cannula 22, which may comprise a Dacron graft or other synthetic material, is coupled to outlet 23 of implantable pump 20.

Figure 2:
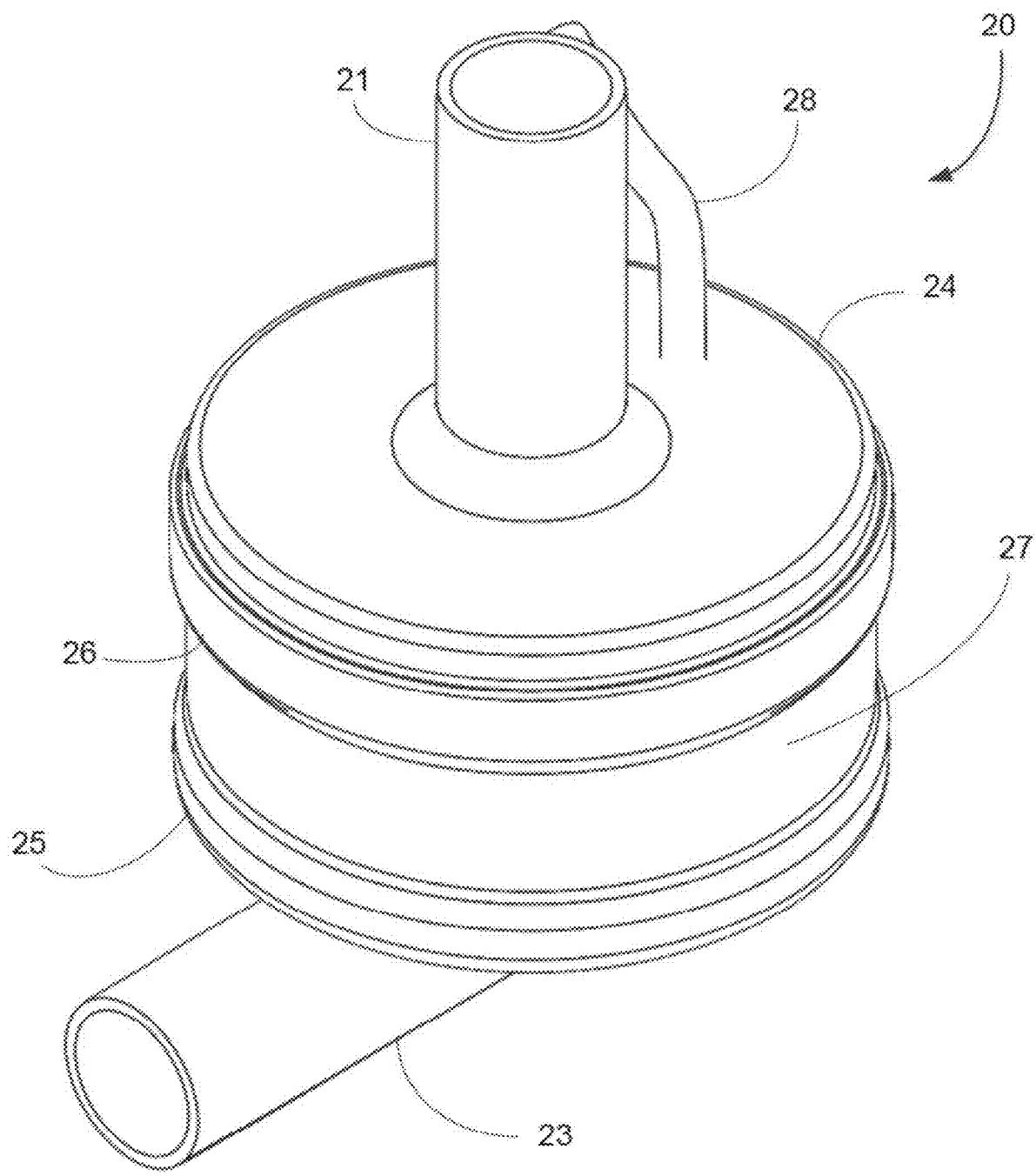
FIG. 2 is a perspective view of the implantable pump of FIG. 1.

Referring now also to FIG. 2, implantable pump 20 in a preferred embodiment consists of upper housing portion 24 joined to lower housing portion 25 along interface 26, for example, by threads or welding, to form fluid tight pump housing 27 that may have a cylindrical shape. Upper housing portion 24 includes inlet cannula 21 and electrical conduit 28 for receiving electrical wires from controller 30 and battery 40. Lower housing portion 25 includes outlet 23 that couples to outlet cannula 22, as shown in FIG. 1. Pump housing 27 is made of a biocompatible material, such as stainless steel, and is sized to be implanted within a patient's chest.

Referring again to FIG. 1, in one embodiment, controller 30 and battery 40 are extracorporeal, and are sized so as to be placed on a belt or garment worn by the patient. Both controller 30 and battery 40 are electrically coupled to implantable pump 20, for example, via cable 29 that extends through a transcutaneous opening in the patient's skin and into electrical conduit 28 of pump housing 27. Illustratively, battery 40 is electrically coupled to controller 30 via cable 41 that is integrated into belt 42. In an alternative embodiment, controller 30 may be enclosed within a biocompatible housing and sized to be implanted subcutaneously in the patient's abdomen. In this alternative embodiment, controller 30 may include a wireless transceiver for bi-directional communications with an extracorporeal programming device and also include a battery that is continuously and inductively charged via extracorporeal battery 40 and an extracorporeal charging circuit. As will be understood, the foregoing alternative embodiment avoids the use of transcutaneous cable 29, and thus eliminates a frequent source of infection for conventional LVAD devices.

Battery 40 preferably comprises a rechargeable battery capable of powering implantable pump 20 and controller 30 for a period of several days, e.g., 3-5 days, before needing to be recharged. Battery 40 may include a separate charging circuit, not shown, as is conventional for rechargeable batteries. Battery 40 preferably is disposed within a housing suitable for carrying on a belt or holster, so as not to interfere with the patient's daily activities.

Programmer 50 may consist of a conventional laptop computer that is programmed to execute programmed software routines, for use by a clinician or medical professional, for configuring and providing operational parameters to controller 30. The configuration and operational parameter data is stored in a memory associated with controller 30 and used by the controller to control operation of implantable pump 20. As described in further detail below, controller 30 directs implantable pump 20 to operate at specific parameters determined by programmer 50. Programmer 50 preferably is coupled to controller 30 via cable 51 only when the operational parameters of the implantable pump are initially set or periodically adjusted, e.g., when the patient visits the clinician.

In accordance with another aspect of the invention, mobile device 60, which may a conventional smartphone, may include an application program for bi-directionally and wirelessly communicating with controller 30, e.g., via WiFi or Bluetooth communications. The application program on mobile device 60 may be programmed to permit the patient to send instructions to controller to modify or adjust a limited number of operational parameters of implantable pump 20 stored in controller 30. Alternatively or in addition, mobile device 60 may be programmed to receive from controller 30 and to display on screen 61 of mobile device 60, data relating to operation of implantable pump 20 or alert or status messages generated by controller 30.

Figure 3A:
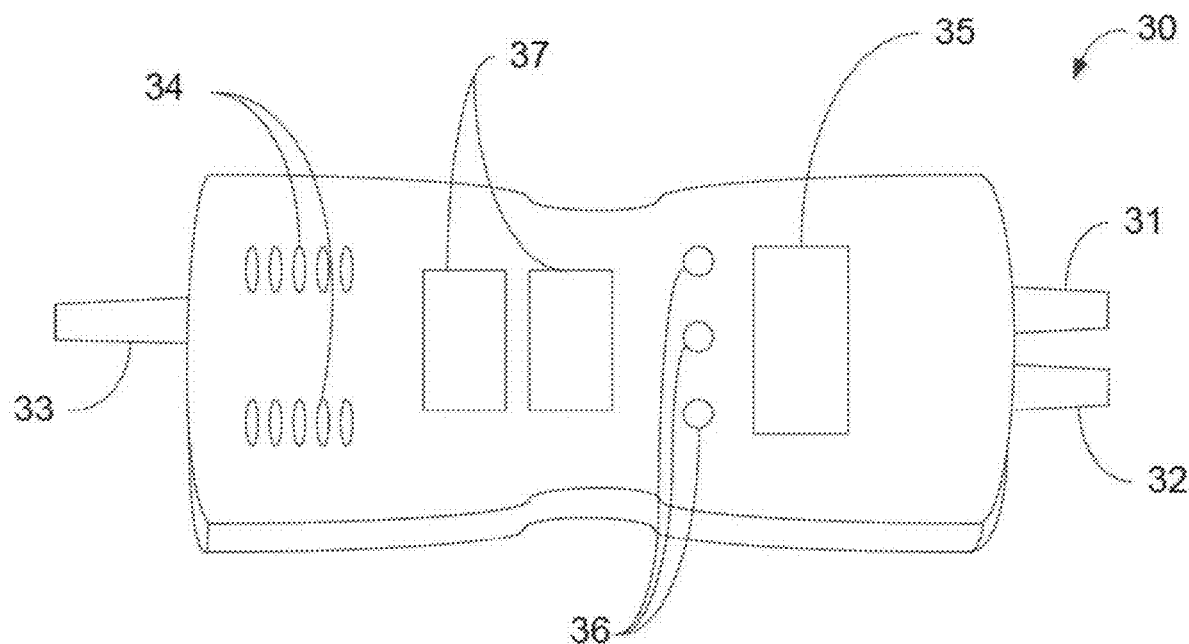
FIGS. 3A and 3B are, respectively, a perspective view and a schematic view of the electronic components of an exemplary embodiment of the controller of the present invention.
Figure 3B:
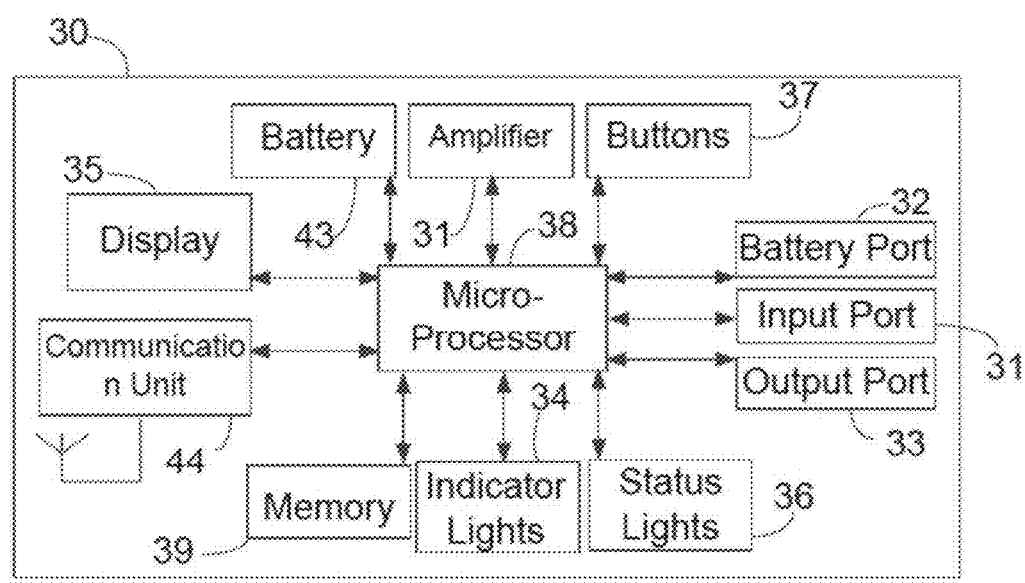

With respect to FIGS. 3A and 3B, controller 30 is described in greater detail. As depicted in FIG. 1, controller 30 may be sized and configured to be worn on the exterior of the patient's body and may be incorporated into a garment such as a belt or a vest. Controller 30 includes input port 31, battery port 32, output port 33, indicator lights 34, display 35, status lights 36 and buttons 37.

Input port 31 is configured to periodically and removably accept cable 51 to establish an electrical connection between programmer 50 and controller 30, e.g., via a USB connection. In this manner, a clinician may couple to controller 30 to set or adjust operational parameters stored in controller 30 for controlling operation of implantable pump. In addition, when programmer 50 is coupled to controller 30, the clinician also may download from controller 30 data relating to operation of the implantable pump, such as actuation statistics, for processing and presentation on display 55 of programmer 50. Alternatively, or in addition, controller 30 may include a wireless transceiver for wirelessly communicating such information with programmer 50. In this alternative embodiment, wireless communications between controller 30 and programmer 50 may be encrypted with an encryption key associated with a unique identification number of the controller, such as a serial number.

Battery port 32 is configured to removably accept cable 41, illustratively shown in FIG. 1 as integrated with belt 42, so that cable 41 routed through the belt and extends around the patient's back until it couples to controller 30. In this manner, battery 40 may be removed from belt 42 and disconnected from controller 30 to enable the patient to periodically replace the battery with a fully charged battery. It is expected that the patient will have available to him or her at least two batteries, so that while one battery is coupled to controller 30 to energize the controller and implantable pump, the other battery may be connected to a recharging station. Alternatively, or in addition, battery port 32 may be configured to accept a cable that is coupled directly to a power supply, such a substantially larger battery/charger combination that permits the patient to remove battery 40 while lying supine in a bed, e.g., to sleep.

Output port 33 is electrically coupled to cable 29, which in turn is coupled to implantable pump 20 through electrical conduit 28 of pump housing 27. Cable 29 provides both energy to energize implantable pump 20 in accordance with the configuration settings and operational parameters stored in controller 30, and to receive data from sensors disposed in implantable pump 20. In one embodiment, cable 29 may comprise an electrical cable having a biocompatible coating and is designed to extend transcutaneously. Cable 29 may be impregnated with pharmaceuticals to reduce the risk of infection, the transmission of potentially hazardous substances or to promote healing where it extends through the patient's skin.

As mentioned above, controller 30 may include indicator lights 34, display 35, status lights 36 and buttons 37. Indicator lights 34 may visually display information relevant to operation of the system, such as the remaining life of battery 40. Display 35 may be a digital liquid crystal display that displays real time pump performance data, physiological data of the patient, such as heart rate, or operational parameters of the implantable pump, such as the target pump pressure or flow rate, etc. When it is determined that certain parameter conditions exceed preprogrammed thresholds, an alarm may be sounded and an alert may be displayed on display 35. Status lights 36 may comprise light emitting diodes (LEDs) that are turned on or off to indicate whether certain functionality of the controller or implantable pump is active. Buttons 37 may be used to wake up display 35, to set or quiet alarms, etc.

With respect to FIG. 3B, the components of the illustrative embodiment of controller 30 of FIG. 3A are described. In addition to the components of controller 30 described in connection with FIG. 3A, controller 30 further includes microprocessor 38, memory 39, battery 43, optional transceiver 44 and amplifier circuitry 45. Microprocessor may be a general purpose microprocessor, for which programming to control operation of implantable pump 20 is stored in memory 39. Memory 39 also may store configuration settings and operational parameters for implantable pump 20. Battery 40 supplies power to controller 30 to provide continuity of operation when battery 40 is periodically swapped out. Optional transceiver 44 to facilitates wireless communication with programmer 50 and/or mobile device 60 via any of a number of well-known communications standards, including BLUETOOTH™, ZigBee, and/or any IEEE 802.11 wireless standard such as Wi-Fi or Wi-Fi Direct. Controller 30 further may include amplifier circuitry 45 for amplifying electrical signals transferred between controller 30 and implantable pump 20.

Figure 4:
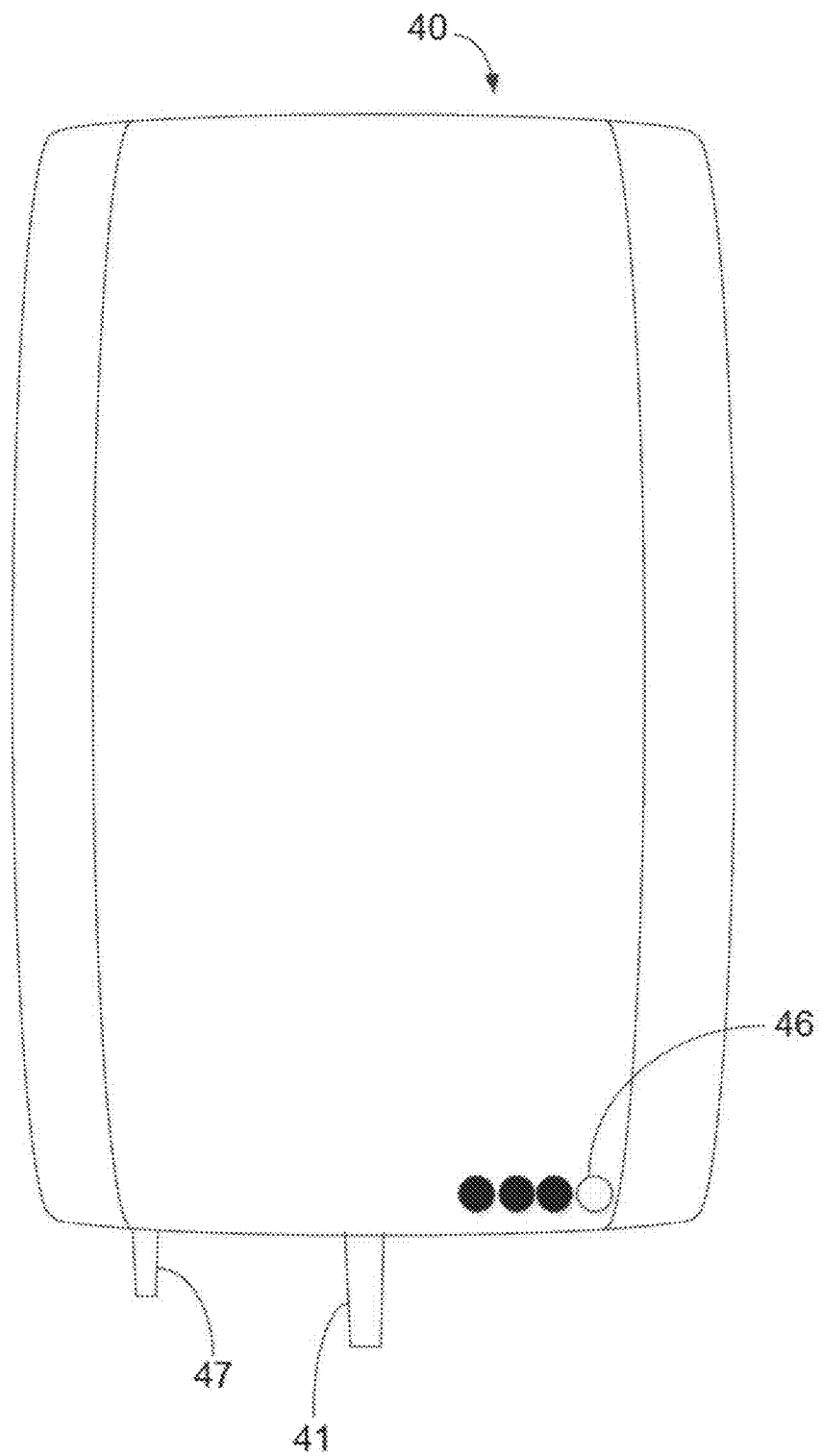
FIG. 4 is a plan view of an extracorporeal battery for use in the pump system of the present invention.

Referring now to FIG. 4, battery 40 is described. Battery 40 provides power to implantable pump 20 and also may provide power to controller 30. Battery 40 may consist of a single battery or a plurality of batteries disposed within a housing, and preferably is sized and configured to be worn on the exterior of the patient's body, such as on belt 42. Battery life indicator 46 may be provided on the exterior of battery 40 to indicate the degree to the remaining charge of the battery. Cable 41 may have one end removably coupled to battery 40 and the other end removably coupled to battery port of controller 30 to supply power to energize implantable pump 20. In one embodiment, battery 40 may be rechargeable using a separate charging station, as is known in the art of rechargeable batteries. Alternatively, or in addition, battery 40 may include port 47 which may be removably coupled to a transformer and cable to permit the battery to be recharged using a conventional residential power outlet, e.g., 120 V, 60 Hz AC power.

Figure 5A:
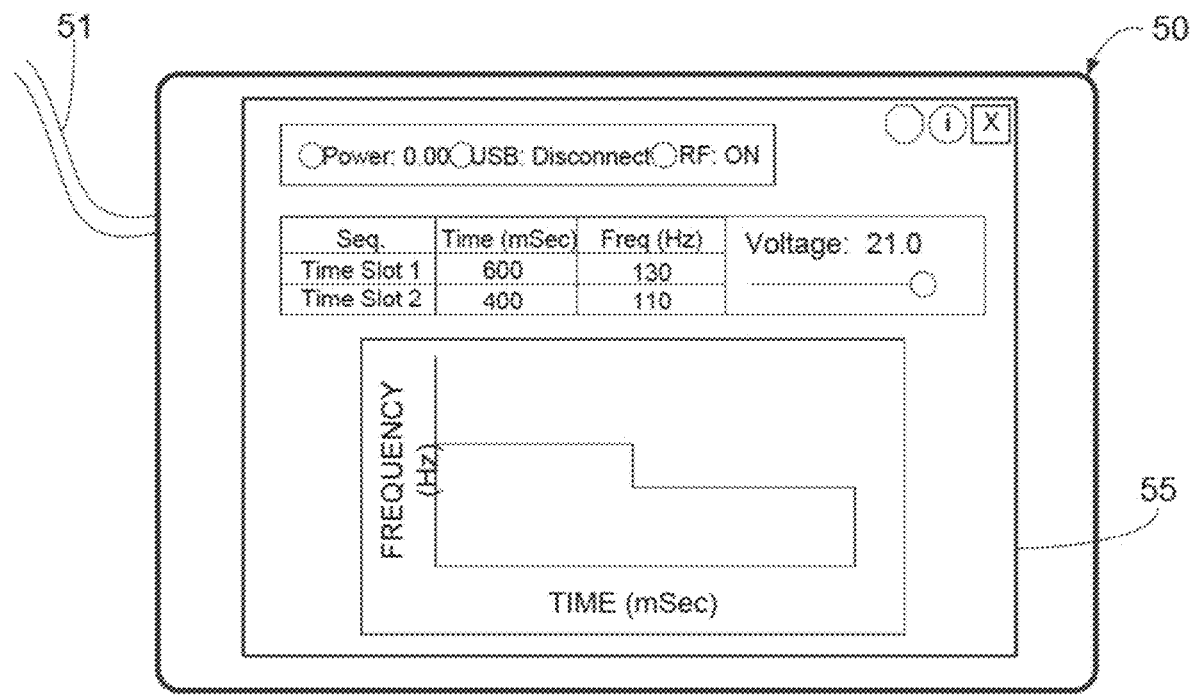
FIGS. 5A and 5B are, respectively, a perspective view and a schematic view of the electronic components of an exemplary embodiment of the programmer of the present invention.
Figure 5B:
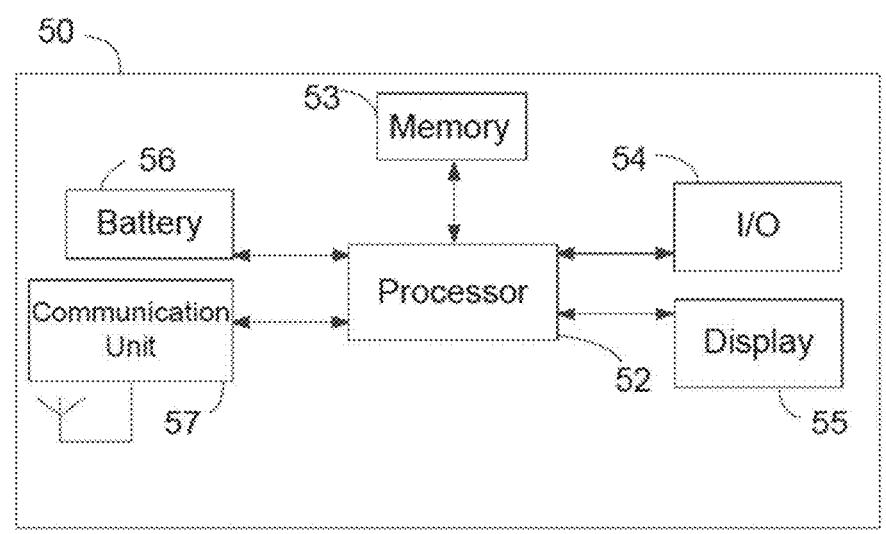

Referring now to FIGS. 5A-5B, programmer 50 is described. Programmer 50 may be conventional laptop loaded with programmed software routines for configuring controller 30 and setting operational parameters that controller 30 uses to control operation of implantable pump 20. As discussed above, programmer 50 typically is located in a clinician's office or hospital, and is coupled to controller 30 via cable 51 or wirelessly to initially set up controller 30, and then periodically thereafter as required to adjust the operational parameters as may be needed. The operation parameters of controller 30 set using the programmed routines of programmer 50 may include but are not limited to applied voltage, pump frequency, pump amplitude, target flow rate, pulsatility, etc. When first implanted, the surgeon or clinician may use programmer 50 to communicate initial operating parameters to controller 30. Following implantation, the patient periodically may return to the clinician's office for adjustments to the operational parameters which may again be made using programmer 50.

Programmer 50 may be any type of conventional personal computer device such as a laptop or a tablet computer having touch screen capability. As illustrated in FIG. 5B, programmer 50 preferably includes processor 52, memory 53, input/output device 54, display 55, battery 56 and communication unit 57. Memory 53 may include the operating system for the programmer, as well as the programmed routines needed to communicate with controller 30. Communication unit 57 may include any of a number of well-known communication protocols, such as BLUETOOTH™, ZigBee, and/or any IEEE 802.11 wireless standard such as Wi-Fi or Wi-Fi Direct. As illustrated in FIG. 5A, the programmed routines used to program and communicate with controller 30 also may provide data for display on the screen of programmer 50 identifying operational parameters with which controller 30 controls implantable pump 20. The programmed routines also may enable programmer 50 to download from controller 30 operational data or physiologic data communicated by the implantable pump and to display that information in real time while the programmer is coupled to the controller via a wired or wireless connection. The transferred data may then be processed and displayed on the screen of programmer 50.

Figure 6:
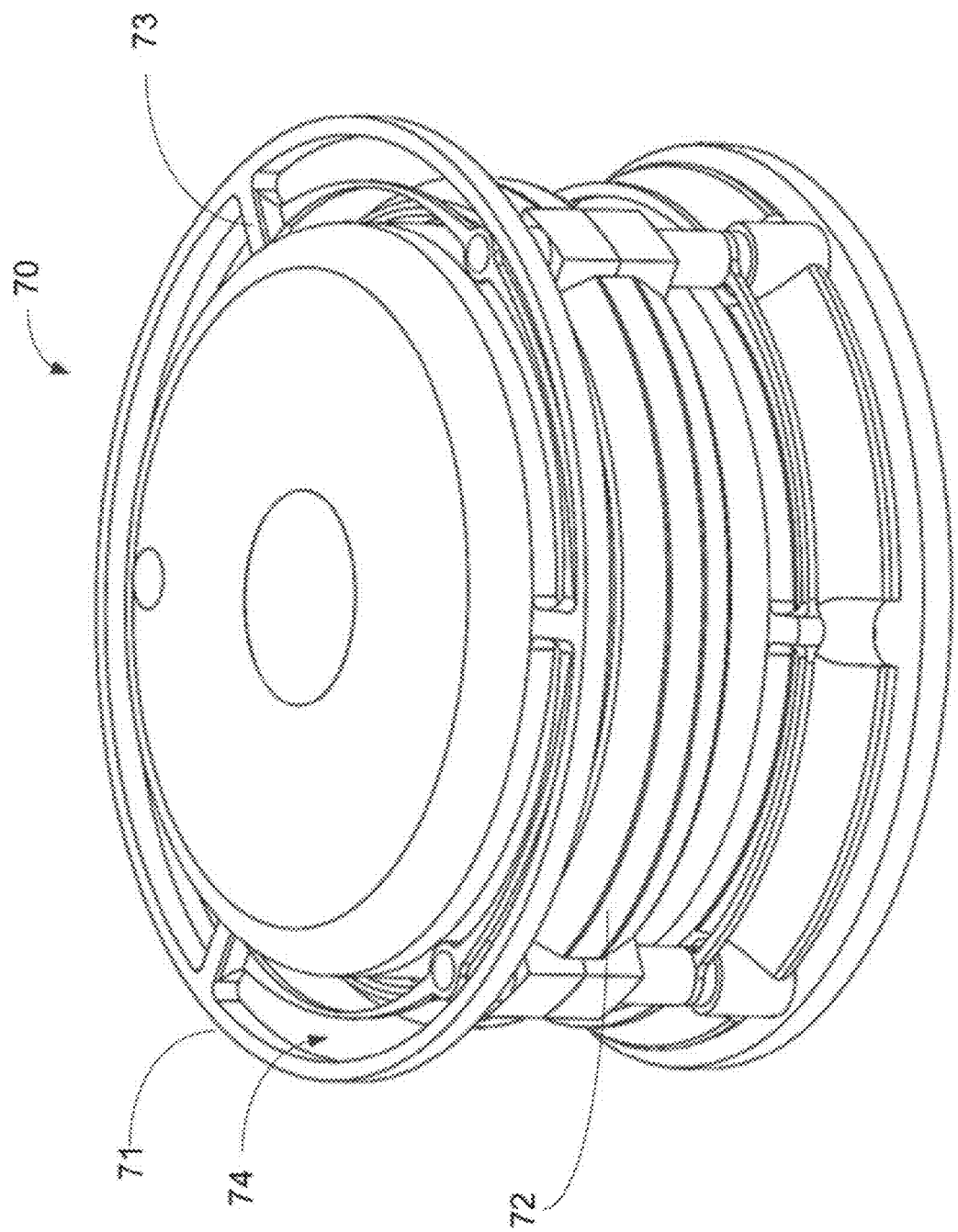
FIG. 6 is a perspective view of the pump assembly of the present invention.
Figure 7:
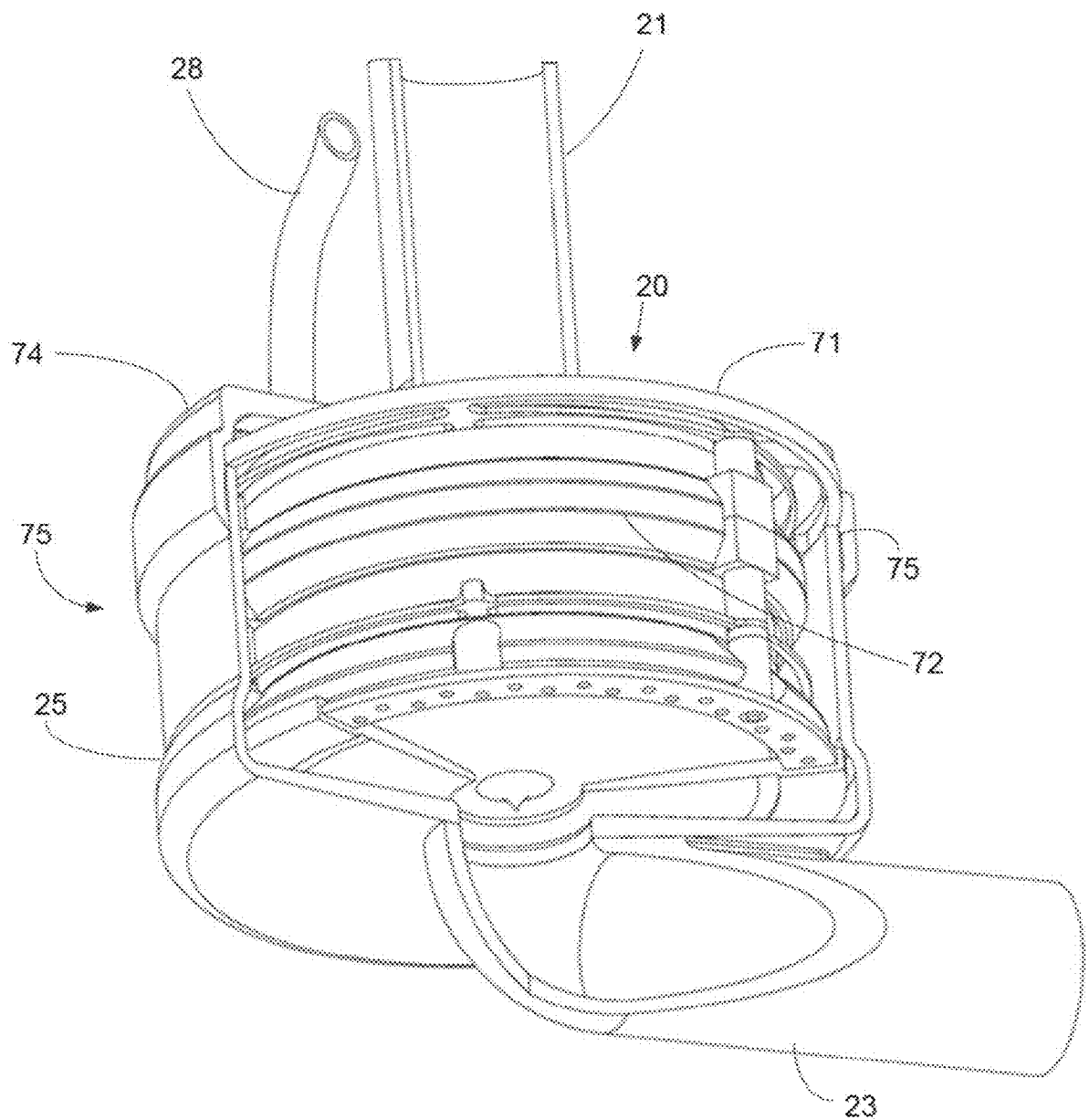
FIG. 7 is a perspective, cut-away view of the implantable pump of the present invention.

Referring now to FIGS. 6 and 7, a preferred embodiment of pump assembly 70 and implantable pump 20 are illustrated. However, it is understood that pump assemblies and implantable pumps, and components included therein, may have different shapes and sizes than those illustrated in FIGS. 6 and 7 without departing from the invention described herein. As is illustrated in FIG. 7, pump assembly 70 is configured to fit within pump housing 27. To fix pump assembly 70 within pump housing 27, pump assembly 70 may include fixation ring 71, which may extend from and around stator assembly 72, and may be captured between upper housing portion 24 and lower housing portion 25 when the housing portions are assembled, as illustrated in FIG. 7. In this manner, stator assembly 72 may be suspended within the pump housing in close-fitting relation to the interior walls of the pump housing. Fixation ring 71 preferably is a rigid annular structure that is disposed concentrically around stator assembly 72, having a larger diameter than stator assembly 72. Fixation ring 71 may be rigidly coupled to stator assembly 72 via struts 73. Struts 73 may create gap 74 between fixation ring 71 and stator assembly 72, which preferably is about 0.05 mm at its most restricted point.

As shown in FIG. 7, pump assembly 70 may be disposed in pump housing 27 such that fixation ring 71 is captured on step 75 formed between upper housing portion 24 and lower housing portion 25. In this manner, stator assembly 72 may be suspended within, and prevented from moving within, pump housing 27. Pump housing 27 preferably is sized and configured to conform to pump assembly 70 such that, stator assembly 72 does not contact the interior of the pump housing at any location other than at fixation ring 71.

Figure 8:
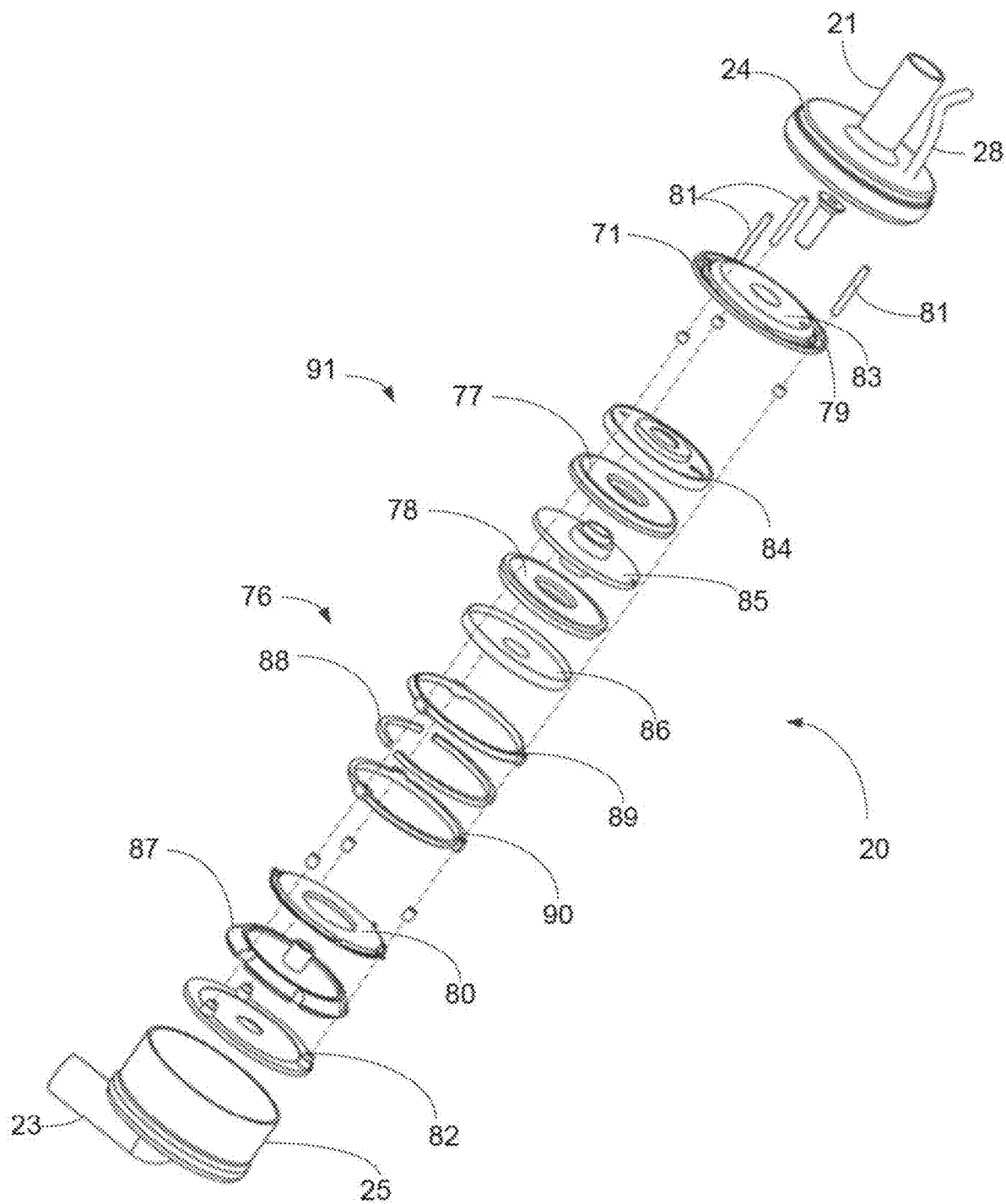
FIG. 8 is an exploded view of the implantable pump of the present invention.

FIG. 8 is an exploded view of implantable pump 20, depicting the arrangement of the internal components of pump assembly 70 arranged between upper housing portion 24 and lower housing portion 25. In particular, pump assembly 70 may comprise stator assembly 72, magnetic ring assembly 76, first electromagnetic coil 77, second electromagnetic coil 78, fixation ring 71, first suspension ring 79, second suspension ring 80, posts 81 and membrane assembly 82. Stator assembly 72 may comprise tapered section 83, electromagnetic coil holder portions 84, 85 and 86, and flanged portion 87. Magnetic ring assembly 76 may comprise magnetic ring 88 and magnetic ring holder portions 89 and 90. First and second electromagnetic coils 77 and 78, together with electromagnetic coil holder portions 84, 85 and 86 may form electromagnet assembly 91. Electromagnet assembly 91 together with stator assembly 72 form an actuator assembly. The actuator assembly together with magnetic ring assembly 76 in turn forms the actuator system of implantable pump 20.

First electromagnetic coil 77 and second electromagnetic coil 78 may be concentrically sandwiched between electromagnetic coil holder portions 84, 85 and 86 to form electromagnet assembly 91. Tapered section 83, which may be coupled to fixation ring 71 and first suspension spring 79, may be located concentrically atop electromagnet assembly 91. Magnetic ring 88 may be disposed with magnetic ring holder portions 89 and 90 to form magnetic ring assembly 76, which may be concentrically disposed for reciprocation over electromagnet assembly 91. Second suspension ring 80 may be disposed concentrically beneath electromagnet assembly 91. Flanged portion 87 may be concentrically disposed below second suspension ring 80. Posts 81 may engage first suspension ring 79, magnetic ring assembly 76 and second suspension ring 80 at equally spaced locations around the actuator assembly. Membrane assembly 82 may be positioned concentrically below flanged portion 87 and engaged with posts 81.

Figure 9:
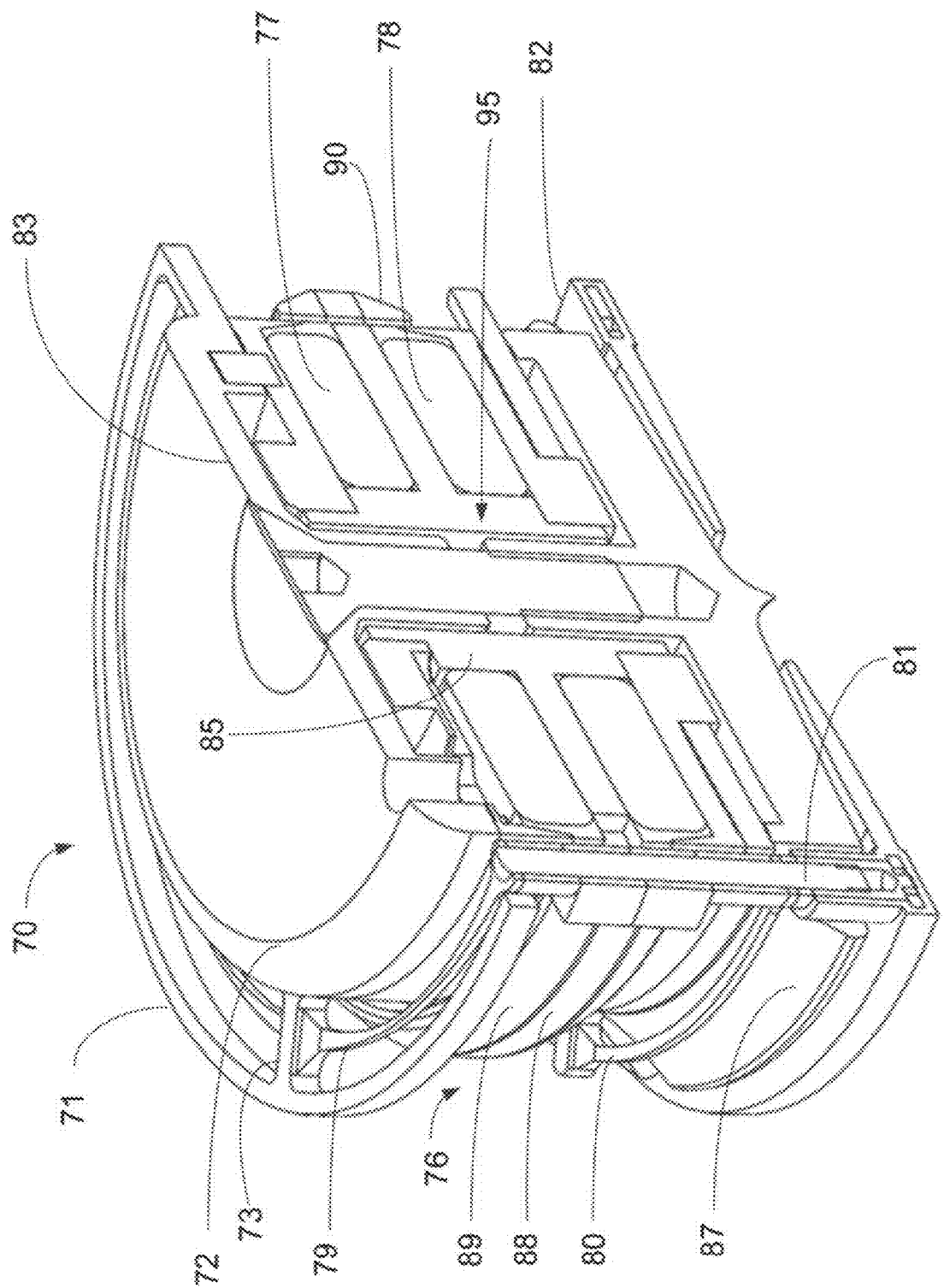
FIG. 9 is a perspective cross-sectional view of the pump assembly of the present invention.

Further details of pump assembly 70 are provided with respect to FIG. 9. Specifically, actuator assembly 95 comprises stator assembly 72 and electromagnet assembly 91, including first and second electromagnetic coils 77 and 78. During use of implantable pump 20, actuator assembly 95 remains stationary relative to pump housing 27. First electromagnetic coil 77 and second electromagnetic coil 78 may be separated by electromagnetic holder portion 85. Controller 30 and battery 40 are electrically coupled to electromagnetic coils 77 and 78 via cable 29 that extends through electrical conduit 28 of pump housing 27 to supply current to electromagnetic coils 77 and 78. First electromagnetic coil 77 and second electromagnetic coil 78 may be in electrical communication with one another or may be configured to operate independently and have separate wired connections to controller 30 and battery 40 via cable 29.

Electromagnetic coils 77 and 78 may be made of any electrically conductive metallic material such as copper and further may comprise of one or more smaller metallic wires wound into a coil. The wires of the electromagnetic coils are insulated to prevent shorting to adjacent conductive material. Other components of pump assembly 70, such as stator assembly 72, preferably also are insulated and/or made of non-conductive material to reduce unwanted transmission of the electrical signal.

Actuator assembly 95 may be surrounded by first suspension ring 79 and second suspension ring 80. Suspension rings 79 and 80 may be annular in shape and fit concentrically around actuator assembly 95. First suspension ring 79 preferably is rigidly affixed to tapered section 83 near a top portion of stator assembly 72 via struts 73 extending from the suspension ring to the stator assembly. As discussed above, struts 73 may also affix fixation ring 71 to stator assembly 72. Fixation ring 71 and first suspension spring 79 may be sized and positioned such that a gap of no less than 0.5 mm exists between first suspension ring 79 and fixation ring 71. Second suspension ring 80 similarly may be rigidly affixed via struts near the bottom of stator assembly 72, below electromagnet assembly 91. Suspension rings 79 and 80 preferably are sized and shaped such that when suspension rings 79 and 80 are positioned surrounding actuator assembly 95, a gap of no less than 0.5 mm exists between actuator assembly 95 and suspension rings 79 and 80.

First suspension ring 79 and second suspension ring 80 may comprise stainless steel having elastic properties and which exhibits a spring force when deflected in a direction normal to the plane of the spring. First suspension ring 79 and second suspension ring 80 may be substantially rigid with respect to forces applied tangential to the suspension ring. In this manner, first suspension ring 79 and second suspension ring 80 may exhibit a spring tension when deformed up and down relative to a vertical axis of the actuator assembly but may rigidly resist movement along any other axis, e.g., tilt or twist movements.

Magnetic ring assembly 76 may be annular in shape and concentrically surrounds actuator assembly 95. Magnetic ring 88 may comprise one or more materials exhibiting magnetic properties such as iron, nickel, cobalt or various alloys. Magnetic ring 88 may be made of a single unitary component or comprise several magnetic components that are coupled together. Magnetic ring assembly 76 may be sized and shaped such that when it is positioned concentrically over actuator assembly 95, a gap of no less than 0.5 mm exists between an outer lateral surface of actuator assembly 95 and an interior surface of magnetic ring assembly 76.

Magnetic ring assembly 76 may be concentrically positioned around actuator assembly 95 between first suspension ring 79 and second suspension ring 80, and may be rigidly coupled to first suspension ring 79 and second suspension ring 80. Magnetic ring assembly 76 may be rigidly coupled to the suspension rings by more than one post 81 spaced evenly around actuator assembly 95 and configured to extend parallel to a central axis of pump assembly 70. Suspension rings 79 and 80 and magnetic ring assembly 76 may be engaged such that magnetic ring assembly 76 is suspended equidistant between first electromagnetic coil 77 and second electromagnetic coil 78 when the suspension rings are in their non-deflected shapes. Each of suspension rings 79 and 80 and magnetic ring holder portions 89 and 90 may include post receiving regions for engaging with posts 81 or may be affixed to posts 81 in any suitable manner that causes suspension rings 79 and 80 and magnetic ring assembly 76 to be rigidly affixed to posts 81. Posts 81 may extend beyond suspension rings 79 and 80 to engage other components, such as flanged portion 87 and membrane assembly 82.

First electromagnetic coil 77 may be activated by controller applying an electrical signal from battery 40 to first electromagnetic coil 77, thus inducing current in the electromagnetic coil and generating a magnetic field surrounding electromagnetic coil 77. The direction of the current in electromagnetic coil 77 and the polarity of magnetic ring assembly 76 nearest electromagnetic coil 77 may be configured such that the first electromagnetic coil magnetically attracts or repeals magnetic ring assembly 76 as desired. Similarly, a magnetic field may be created in second electromagnetic coil 78 by introducing a current in the second electromagnetic coil. The direction of the current in second electromagnetic coil 78 and the polarity of magnetic ring assembly 76 nearest the second electromagnetic coil also may be similarly configured so that first electromagnetic coil 77 magnetically attracts or repels magnetic ring assembly 76 when an appropriate current is induced in second electromagnetic coil 78.

Because magnetic ring assembly 76 may be rigidly affixed to posts 81, which in turn may be rigidly affixed to first suspension ring 79 and second suspension ring 80, the elastic properties of the suspension rings permit magnetic ring assembly 76 to move up towards first electromagnetic coil 77 or downward toward second electromagnetic coil 78, depending upon the polarity of magnetic fields generated by the electromagnetic rings. In this manner, when magnetic ring assembly 76 experiences an upward magnetic force, magnetic ring assembly 76 deflects upward towards first electromagnetic coil 77. As posts 81 move upward with magnetic ring assembly 76, posts 81 cause the suspensions rings 79 and 80 to elastically deform, which creates a spring force opposite to the direction of movement. When the magnetic field generated by the first electromagnetic coil collapses, when the electrical current ceases, this downward spring force causes the magnetic ring assembly to return to its neutral position. Similarly, when magnetic ring assembly 76 is magnetically attracted downward, magnetic ring assembly 76 deflects downward towards second electromagnetic ring 78. As posts 81 move downward with magnetic ring assembly 76, posts 81 impose an elastic deformation of the first and second suspension rings, thus generating a spring force in the opposite direction. When the magnetic field generated by the second electromagnetic ring collapses, when the electrical current ceases, this upward spring force causes the magnetic ring assembly to again return to its neutral position.

Electromagnetic coils 77 and 78 may be energized separately, or alternatively, may be connected in series to cause the electromagnetic coils to be activated simultaneously. In this configuration, first magnetic coil may be configured to experience a current flow direction opposite that of the second electromagnetic coil. Accordingly, when current is induced to first electromagnetic coil 77 to attract magnetic ring assembly 76, the same current is applied to second electromagnetic coil 78 to induce a current that causes second electromagnetic coil 78 to repel magnetic ring assembly 76. Similarly, when current is induced to second electromagnetic coil 78 to attract magnetic ring assembly 76, the current applied to first electromagnetic coil 77 causes the first electromagnetic coil to repel magnetic ring assembly 76. In this manner, electromagnetic coils 77 and 78 work together to cause deflection of magnetic ring assembly 76.

By manipulating the timing and intensity of the electrical signals applied to the electromagnetic coils, the frequency at which magnetic ring assembly 76 deflects towards the first and second electromagnetic coils may be altered. For example, by alternating the current induced in the electromagnetic coils more frequently, the magnetic ring assembly may be caused to cycle up and down more times in a given period. By increasing the amount of current, the magnetic ring assembly may be deflected at a faster rate and caused to travel longer distances.

Alternatively, first electromagnetic coil 77 and second electromagnetic coil 78 may be energized independently. For example, first electromagnetic coil 77 and second electromagnetic coil 78 may be energized at varying intensities; one may be coordinated to decrease intensity as the other increases intensity. In this manner, intensity of the signal applied to second electromagnetic coil 78 to cause downward magnetic attraction may simultaneously be increased as the intensity of the signal applied to first electromagnetic coil 77 causes an upward magnetic attraction that decreases.

In accordance with one aspect of the invention, movements of magnetic ring assembly 76 may be translated to membrane assembly 82 which may be disposed concentrically below stator assembly 72. Membrane assembly 82 preferably is rigidly attached to magnetic ring assembly 76 by posts 81. In the embodiment depicted in FIG. 9, posts 81 may extend beyond second suspension ring 80 and coupled to membrane assembly 82.

Figure 10:
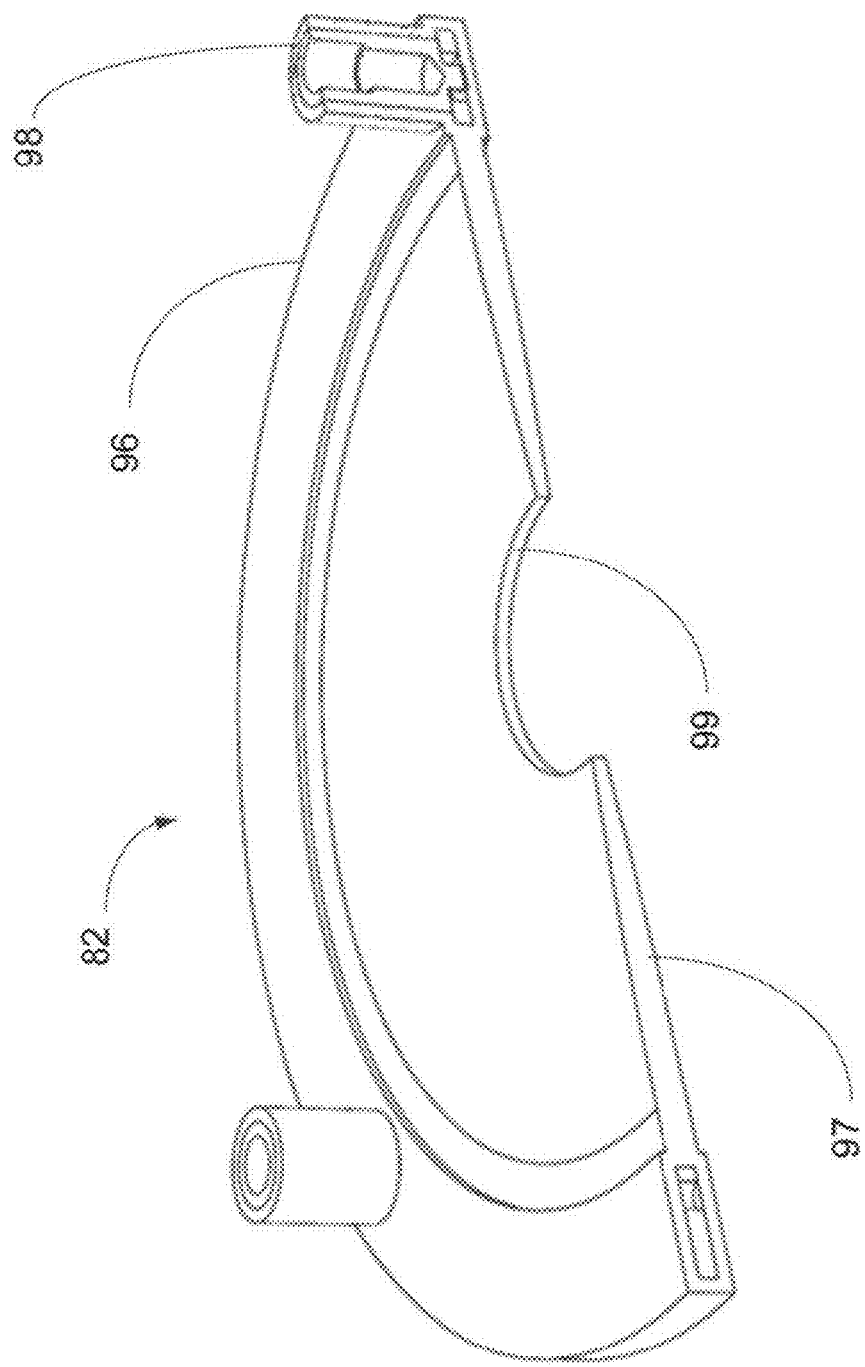
FIG. 10 is a perspective cross-sectional view of the membrane assembly of the present invention.

Referring now to FIG. 10, one embodiment of membrane assembly 82 is described in greater detail. Membrane assembly 82 may comprise rigid membrane ring 96 and membrane 97. Rigid membrane ring 96 exhibits rigid properties under typical forces experienced during the full range of operation of the present invention. Post reception sites 98 may be formed into rigid membrane ring 96 to engage membrane assembly 82 with posts 81. Alternatively, posts 81 may be attached to rigid membrane ring 96 in any other way which directly translates the motion of magnetic ring assembly 76 to rigid membrane ring 96. Rigid membrane ring 96 may be affixed to membrane 97 and hold the membrane in tension. Membrane 97 may be molded directly onto rigid membrane ring 96 or may be affixed to rigid membrane ring 96 in any way that holds membrane 97 uniformly in tension along its circumference. Membrane 97 alternatively may include a flexible pleated structure where it attaches to rigid membrane ring 96 to increase the ability of the membrane to move where the membrane is affixed to rigid membrane ring 96. Membrane 97 may further include circular aperture 99 disposed in the center of the membrane.

In a preferred embodiment, membrane 97 has a thin, planar shape and is made of an elastomer having elastic properties and good durability. Alternatively, membrane 97 may have a uniform thickness from the membrane ring to the circular aperture. As a yet further alternative, membrane 97 may vary in thickness and exhibit more complex geometries. For example, as shown in FIG. 10, membrane 97 may have a reduced thickness as the membrane extends from rigid membrane ring 96 to circular aperture 99. Alternatively, or in addition to, membrane 97 may incorporate metallic elements such as a spiral spring to enhance the spring force of the membrane in a direction normal to plane of the membrane, and this spring force may vary radially along the membrane. In yet another embodiment, membrane 97 may be pre-formed with an undulating shape.

Figure 11:
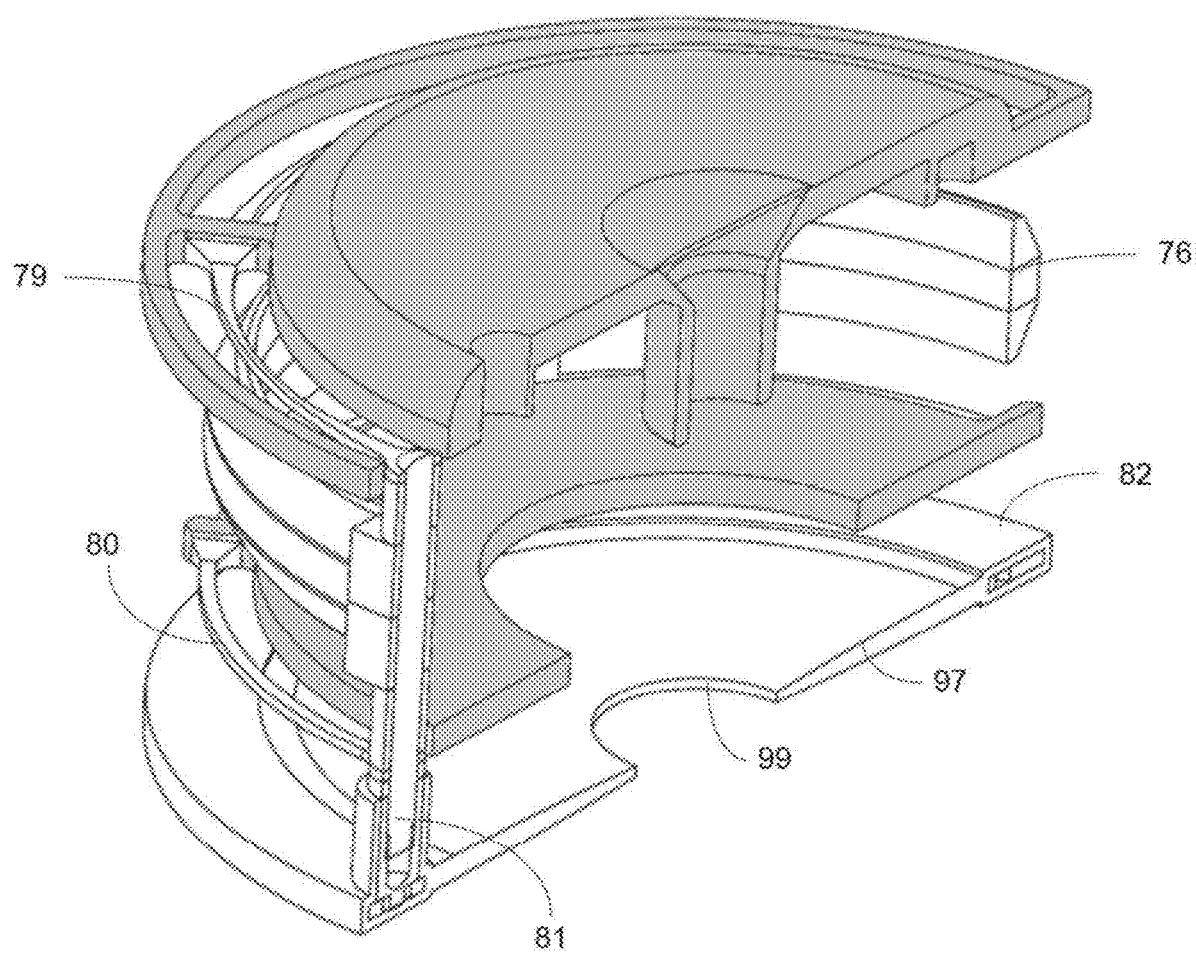
FIG. 11 is a perspective cross-sectional view of the moving components of the pump assembly according to a first embodiment of the present invention.

FIG. 11 depicts moving portions of the embodiment of pump assembly 70 shown in FIGS. 6-9 as non-grayed out elements. Non-moving portions of the pump assembly, including actuator assembly 95 and electromagnet assembly 91 (partially shown) may be fixed to pump housing 27 by fixation ring 71. Moving portions of pump assembly 70 may include posts 81, first suspension spring 79, magnetic ring assembly 76, second suspension spring 80 and membrane assembly 82. As magnetic ring assembly 76 moves up and down, the movement is rigidly translated by posts 81 to membrane assembly 82. Given the rigidity of the posts, when magnetic ring assembly 76 travels a certain distance upward or downward, membrane assembly 82 may travel the same distance. For example, when magnetic ring assembly 76 travels 2 mm from a position near first electromagnetic coil 77 to a position near second electromagnetic coil 78, membrane assembly 82 may also travel 2 mm in the same direction. Similarly, the frequency at which magnetic ring assembly 76 traverses the space between the first and second electromagnetic coils may be the same frequency at which membrane assembly 82 travels the same distance.

Figure 12:
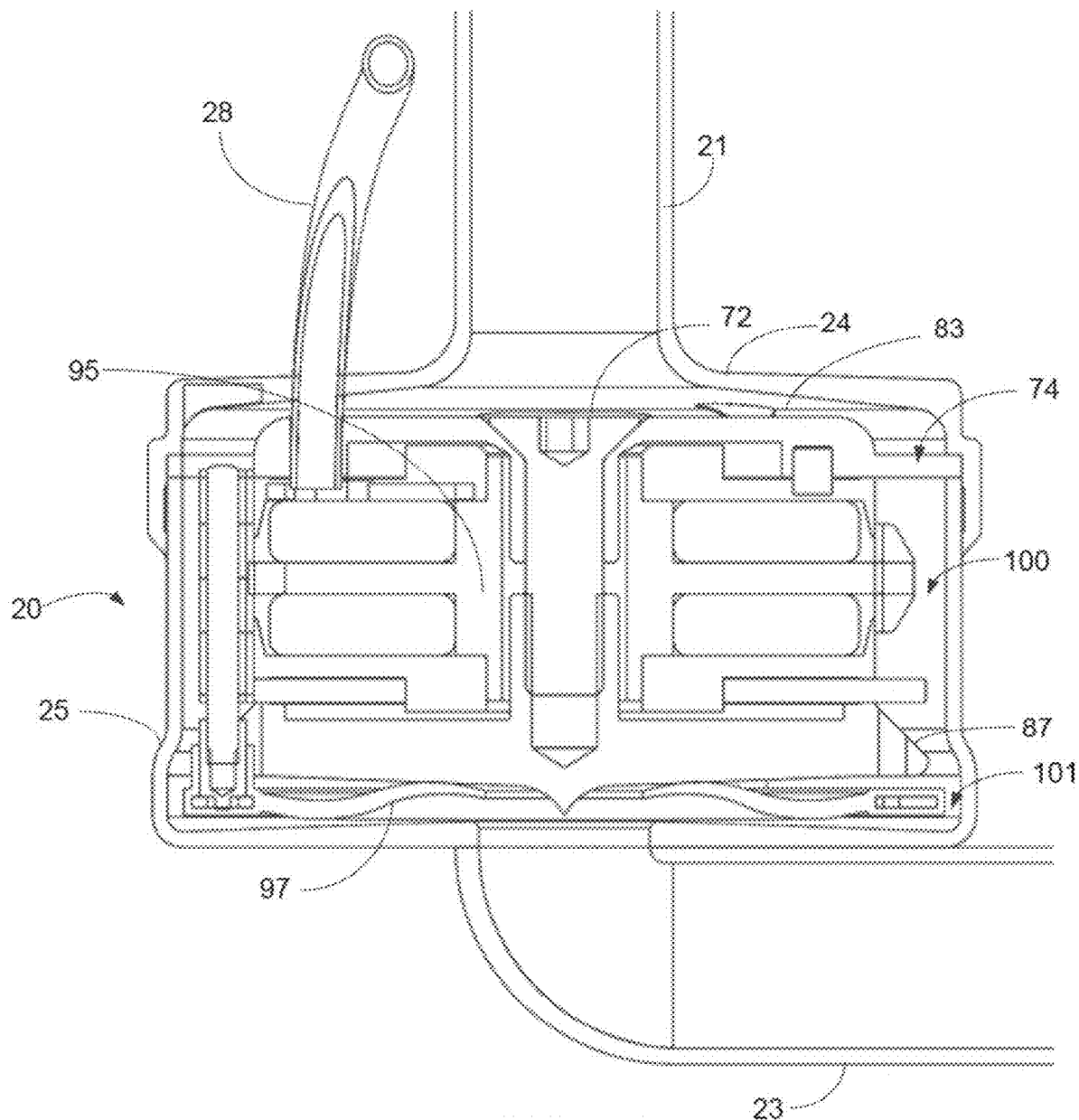
FIG. 12 is a cross-sectional view of the implantable pump of the present invention.

Referring now to FIG. 12, in the embodiment of implantable pump 20 described in FIGS. 6-9, blood may enter implantable pump 20 from the left ventricle through inlet cannula 21 and flow downward along pump assembly 70 into delivery channel 100, defined by the interior surface of pump housing 27 and exterior of pump assembly 70. Delivery channel 100 begins at the top of stator assembly 72 and extends between tapered section 83 and the interior of pump housing 27. As the blood moves down tapered section 83, it is directed through gap 74 and into a vertical portion of delivery channel 100 in the area between pump housing 27 and actuator assembly 95, and including in the gap between magnetic ring assembly 76 and electromagnet assembly 91. Delivery channel 100 extends down to flanged portion 87 of stator assembly 72, which routes blood into flow channel 101, within which membrane assembly 82 is suspended. By directing blood from inlet cannula 21 through delivery channel 100 to flow channel 101, delivery channel 100 delivers blood to membrane assembly 82. By actuating electromagnetic coils 77 and 78, membrane 97 may be undulated within flow channel 101 to induce wavelike formations in membrane 97 that move from the edge of the membrane towards circular aperture 99. Accordingly, when blood is delivered to membrane assembly 82 from delivery channel 100, it may be propelled radially along both the top and bottom of membrane 97 towards circular aperture 99, and from there out of outlet 23.

In accordance with one aspect of the present invention, the undulating membrane pump described herein avoids thrombus formation by placing all moving parts directly within the primary flow path, thereby reducing the risk of flow stagnation. Specifically, the moving components depicted in FIG. 11, including magnetic ring assembly 76, suspension rings 79 and 80, posts 81 and membrane assembly 82 all are located within delivery channel 100 and flow channel 101. Flow stagnation may further be avoided by eliminating secondary flow paths that may experience significantly slower flow rates.

Turning now to FIGS. 13 and 14, a lower portion of implantable pump 20, including flanged portion 87, membrane assembly 82 and lower housing portion 23 is shown. Delivery channel 100 may be in fluid communication with membrane assembly 82 and flow channel 101 which is defined by a bottom surface of flanged portion 87 and the interior surface of lower housing portion 25. Flanged portion 87 may comprise feature 102 that extends downward as the bottom of flanged portion 87 moves radially inward. The interior surface of lower housing portion 25 may also slope upward as it extends radially inward. The combination of the upward slope of the interior surface of lower housing portion 25 and the bottom surface of flanged portion 87 moving downward narrows flow channel 101 as the channel moves radially inwards from delivery channel 100 to circular aperture 99 of membrane 97, which is disposed about pump outlet 23.

As explained above, membrane assembly 82 may be suspended by posts 81 within flow channel 101 below the bottom surface of flanged portion 87 and above the interior surface of lower housing portion 25. Membrane assembly 82 may be free to move up and down in the vertical direction within flow channel 101, which movement is constrained only by suspension rings 79 and 80. Membrane assembly 82 may be constrained from twisting, tilting or moving in any direction in flow channel 101 other than up and down by rigid posts 81 and by the suspension rings.

Flow channel 101 is divided by membrane 97 into an upper flow channel and a lower flow channel by membrane 97. The geometry of membrane 97 may be angled such that when membrane assembly 82 is at rest, the top surface of membrane 97 is parallel to the bottom surface of flanged portion 87 and the bottom surface of membrane 97 is parallel to the opposing surface of lower housing portion 25. Alternatively, membrane 97 may be sized and shaped such that when membrane assembly 82 is at rest, the upper and lower flow channels narrow as they move radially inward from delivery channel 100 to circular aperture 99 in membrane 97.

Referring now also to FIG. 14, as rigid membrane ring 96 is caused by posts 81 to move up and down in flow channel 101, the outermost portion of membrane 97 nearest rigid membrane ring 96, moves up and down with rigid membrane ring 96. Membrane 97, being flexible and having elastic properties, gradually translates the up and down movement of the membrane portion nearest rigid membrane ring 96 along membrane 97 towards circular aperture 99. This movement across flexible membrane 97 causes wave-like deformations in the membrane which may propagate inwards from rigid membrane ring 96 towards aperture 99.

The waves formed in the undulating membrane may be manipulated by changing the speed at which rigid membrane ring 96 moves up and down as well as the distance rigid membrane ring 96 moves up and down. As explained above, the amplitude and frequency at which rigid membrane ring 96 moves up and down is determined by the amplitude and frequency at which magnetic ring assembly 76 reciprocates over electromagnet assembly 91 Accordingly, the waves formed in the undulating membrane may be adjusted by changing the frequency and amplitude at which magnetic ring assembly 76 is reciprocated.

When blood is introduced into flow channel 101 from delivery channel 100, the undulations in membrane 97 cause blood to be propelled toward circular aperture 99 and out of pump housing 27 via outlet 23. The transfer of energy from the membrane to the blood is directed radially inward along the length of the membrane towards aperture 99, and propels the blood along the flow channel towards outlet 23 along both sides of membrane 97.

For example, when rigid membrane ring 96 moves downward in unison with magnetic ring assembly 76, the upper portion of flow channel 101 near delivery channel 100 expands, causing blood from delivery channel 100 to fill the upper portion of the flow channel near the outer region of membrane 97. As rigid membrane ring 96 moves upward, the upper portion of flow channel 101 begins to narrow near rigid membrane ring 96, causing wave-like deformations to translate across the membrane. As the wave propagates across membrane 97, blood in the upper portion of flow channel 101 is propelled towards circular aperture and ultimately out of pump housing 27 through outlet 23. Simultaneously, as rigid membrane ring 96 moves upwards, the lower portion of flow channel 101 nearest the outer portion of membrane 97 begins to enlarge, allowing blood from delivery channel 100 to flow into this region. Subsequently, when rigid membrane ring 96 is again thrust downwards, the region of lower portion of flow channel 101 nearest outer portion of membrane 97 begins to narrow, causing wave-like deformations to translate across the membrane that propel blood towards outlet 23.

By manipulating the waves formed in the undulating membrane by changing the frequency and amplitude at which magnetic ring assembly 76 moves up and down, the pressure gradient within flow channel 101 and ultimately the flow rate of the blood moving through flow channel 101 may be adjusted. Appropriately controlling the movement of magnetic ring assembly 76 permits oxygen-rich blood to be effectively and safely pumped from the left ventricle to the aorta and throughout the body as needed.

In addition to merely pumping blood from the left ventricle to the aorta, implantable pump 20 of the present invention may be operated to closely mimic physiologic pulsatility, without loss of pump efficiency. In the embodiment detailed above, pulsatility may be achieved nearly instantaneously by changing the frequency and amplitude at which magnetic ring assembly 76 moves, to create a desired flow output, or by ceasing movement of the magnetic ring assembly for a period time to create a period of low or no flow output. Unlike typical rotary pumps, which require a certain period of time to attain a set number of rotations per minute to achieve a desired fluid displacement and pulsatility, implantable pump 20 may achieve a desired flow output nearly instantaneously and similarly may cease output nearly instantaneously due to the very low inertia generated by the small moving mass of the moving components of the pump assembly. The ability to start and stop on-demand permits rapid changes in pressure and flow. Along with the frequency and amplitude, the duty cycle, defined by the percentage of time membrane 97 is excited over a set period of time, may be adjusted to achieve a desired flow output and pulsatility, without loss of pump efficiency. Even holding frequency and amplitude constant, flow rate may be altered by manipulating the duty cycle between 0 and 100%.

In accordance with another aspect of the invention, controller 30 may be programmed by programmer 50 to operate at selected frequencies, amplitudes and duty cycles to achieve a wide range of physiologic flow rates and with physiologic pulsatilities. For example, programmer 50 may direct controller 30 to operate implantable pump 20 at a given frequency, amplitude and/or duty cycle during a period of time when a patient is typically sleeping and may direct controller 30 to operate implantable pump 20 at a different frequency, amplitude and or duty cycle during time periods when the patient is typically awake. Controller 30 or implantable pump also may include an accelerometer or position indicator to determine whether the patient is supine or ambulatory, the output of which may be used to move from one set of pump operating parameters to another. When the patient experiences certain discomfort or a physician determines that the parameters are not optimized, physician may alter one or more of at least frequency, amplitude and duty cycle to achieve the desired functionality. Alternatively, controller 30 or mobile device 60 may be configured to alter one or more of frequency, amplitude and duty cycle to suit the patient's needs.

Implantable pump 20 further may comprise one or more additional sensors for adjusting flow output and pulsatility according to the demand of the patient. Sensors may be incorporated into implantable pump 20 or alternatively or in addition to may be implanted elsewhere in or on the patient. The sensors preferably are in electrical communication with controller 30, and may monitor operational parameters that measure the performance of implantable pump 20 or physiological sensors that measure physiological parameters of the patients such as heart rate or blood pressure. By using one or more physiological sensors, pulsatile flow may be synchronized with a cardiac cycle of the patient by monitoring blood pressure or muscle contractions, for example, and synchronizing the duty cycle according to the sensed output.

Controller 30 may compare physiological sensor measurements to current implantable pump output. If it is determined by analyzing sensor measurements that demand exceeds current output, frequency, amplitude and/or duty cycle may be automatically adjusted to meet current demand. Similarly, the controller may determine that current output exceeds demand and thus alter output by changing frequency, amplitude and/or duty cycle. Alternatively, or in addition to, when it is determined that demand exceeds current output, an alarm may sound from controller 30. Similarly, operational measurements from operational sensors may be compared against predetermined thresholds and where measurements exceed predetermined thresholds or a malfunction is detected, an alarm may sound from controller 30.

Implantable pump 20 is sized and shaped to produce physiological flow rates, pressure gradients and pulsatility at an operating point at which maximum efficiency is achieved. Specially, implantable pump 20 may be sized and shaped to produce physiological flow rates ranging from 4 to 6 liters per minute at pressure gradients lower than a threshold value associated with hemolysis. Also, to mimic a typical physiological pulse of 60 beats per minute, implantable pump 20 may pulse about once per second. To achieve such pulsatility, a duty cycle of 50% may be utilized with an "on" period of 0.5 seconds and an "off" period of 0.5 seconds. For a given system, maximum efficiency at a specific operating frequency, amplitude and voltage may be achieved while producing a flow rate of 4 to 6 liters per minute at a duty cycle of 50% by manipulating one or more of the shape and size of blood flow channels, elastic properties of the suspension rings, mass of the moving parts, membrane geometries, and elastic properties and friction properties of the membrane. In this manner, implantable pump 20 may be designed to produce desirable physiological outputs while continuing to function at optimum operating parameters.

By adjusting the duty cycle, implantable pump 20 may be configured to generate a wide range of output flows at physiological pressure gradients. For example, for an exemplary LVAD system configured to produce 4 to 6 liters per minute at a duty cycle of 50%, optimal operating frequency may be 120 Hz. For this system, flow output may be increased to 10 liters per minute or decreased to 4 liters per minute, for example, by changing only the duty cycle. As duty cycle and frequency operate independent of one another, duty cycle may be manipulated between 0 and 100% while leaving the frequency of 120 Hz unaffected.

The implantable pump system described herein, tuned to achieve physiological flow rates, pressure gradients and pulsatility, also avoids hemolysis and platelet activation by applying low to moderate shear forces on the blood, similar to those exerted by a healthy heart. The moving components are rigidly affixed to one another and do not incorporate any parts that would induce friction, such as mechanical bearings or gears. In the embodiment detailed above, delivery channel 100 may be sized and configured to also avoid friction between moving magnetic ring assembly 76, suspension rings 79 and 80, posts 81 and lower housing portion 25 by sizing the channel such that clearances of at least 0.5 mm are maintained between all moving components. Similarly, magnetic ring assembly 76, suspension rings 79 and 80, and posts 81 all may be offset from stator assembly 72 by at least 0.5 mm to avoid friction between the stator assembly and the moving parts.

Figure 15A:
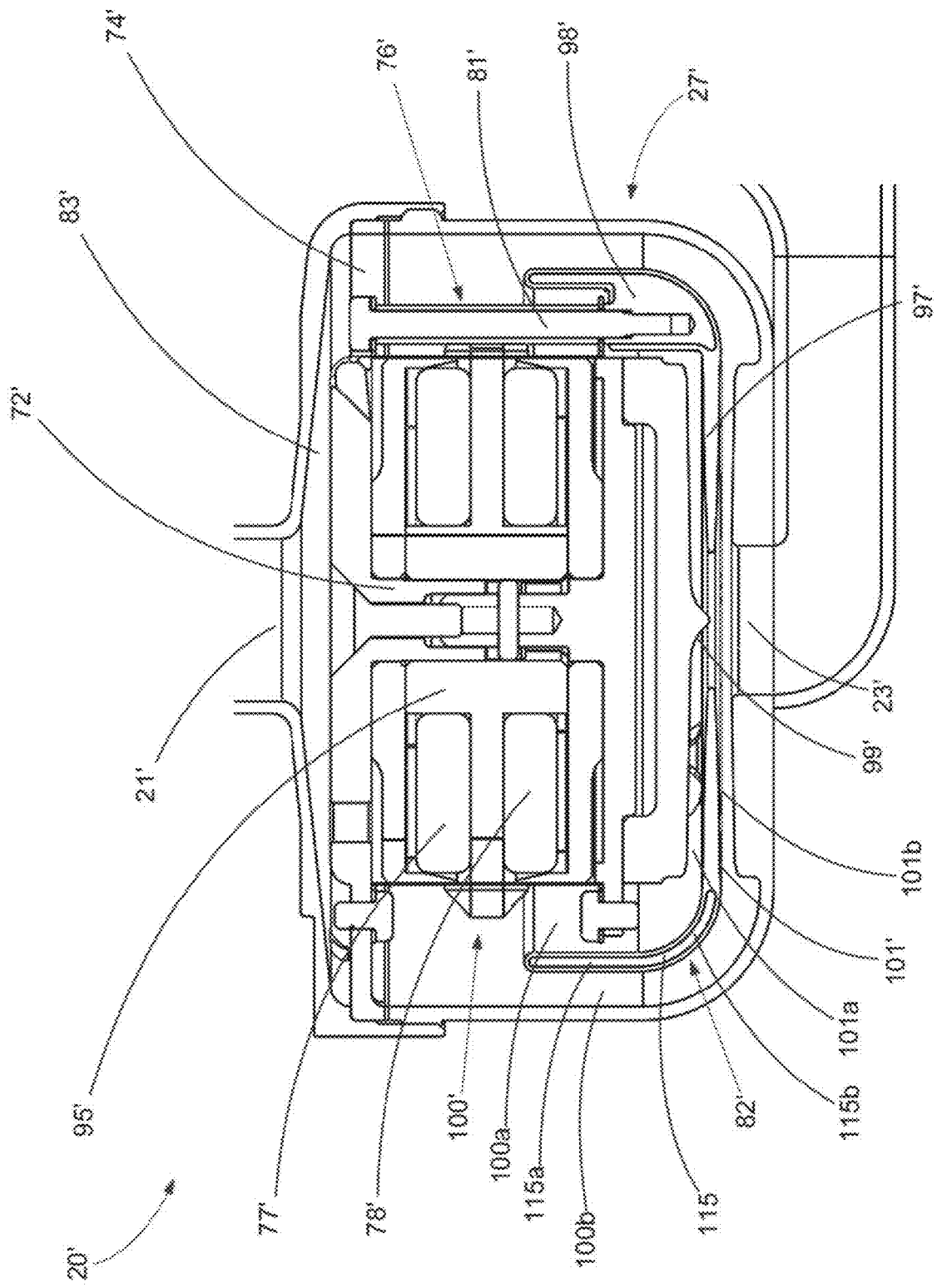
FIG. 15A is a cross-sectional view of an alternative exemplary embodiment of an implantable pump of the present invention with improved hydraulic performance for use in the pump system of FIG. 1.
Figure 15B:
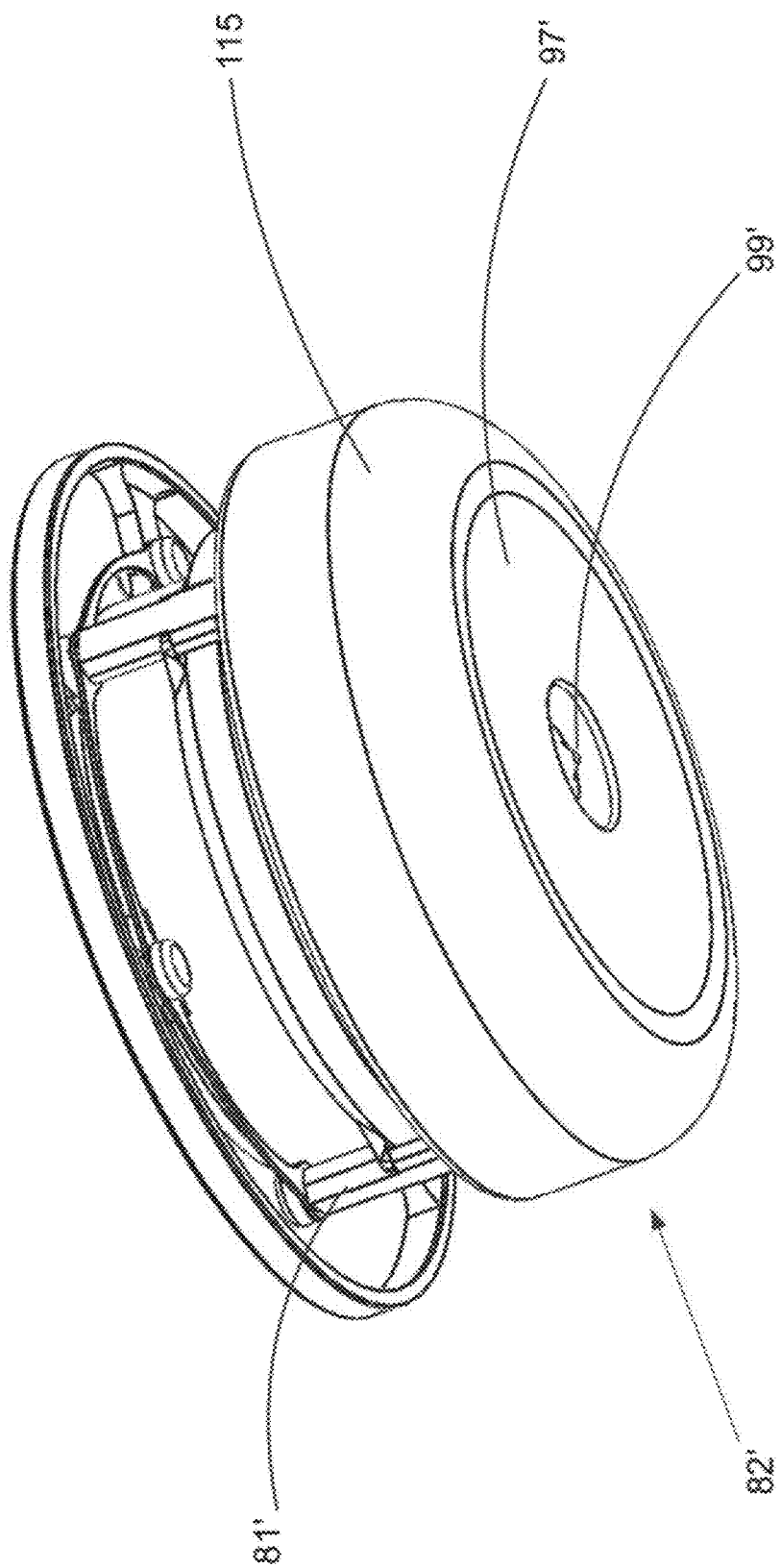
FIG. 15B is a perspective view of the implantable pump of FIG. 15A.

Referring now to FIGS. 15A and 15B, an alternative exemplary embodiment of the pump assembly of the present invention is described. Implantable pump 20' is constructed similar to implantable pump 20 described in FIGS. 7, 8, and 12, in which similar components are identified with like-primed numbers. Implantable pump 20' is distinct from implantable pump 20 in that membrane assembly 82' includes skirt 115 coupled to membrane 97'. Skirt illustratively includes first portion 115a and second portion 115b. First portion 115a of skirt 115 extends upward within delivery channel 100' toward inlet 21' in a first direction, e.g., parallel to the longitudinal axis of stator assembly 72' and/or to the central axis of pump housing 27'. Second portion 115b of skirt 115 curves toward outlet 23' such that second portion 115b is coupled to membrane 97' so that membrane 97' is oriented in a second direction, e.g., perpendicular to first portion 115a of skirt 115. For example, skirt 115 may have a J-shaped cross-section, such that first portion 115a forms a cylindrical-shaped ring about stator assembly 72' and second portion 115b has a predetermined radius of curvature which allows blood to flow smoothly from delivery channel 100' across skirt 115 to the outer edge of membrane 97' and into flow channel 101', while reducing stagnation of blood flow. Skirt 115 breaks flow recirculation of blood within delivery channel 100' and improves hydraulic power generated for a given frequency while minimizing blood damage. In addition, the J-shape of skirt 115 around stator assembly 72' is significantly more stiff than a planar rigid membrane ring, thereby reducing flexing and fatigue, as well as drag as the blood moves across membrane 97'.

Skirt 115 exhibits rigid properties under typical forces experienced during the full range of operation of the present invention and may be made of a biocompatible metal, e.g., titanium. Skirt 115 is preferably impermeable such that blood cannot flow through skirt 115. Post reception sites 98' may be formed into skirt 115 to engage membrane assembly 82' with posts 81'. Alternatively, posts 81' may be attached to skirt 115 in any other way which directly translates the motion of magnetic ring assembly 76' to skirt 115.

As magnetic ring assembly 76' moves up and down, the movement is rigidly translated by posts 81' to J-shape of skirt 115 of membrane assembly 82'. Given the rigidity of the posts, when magnetic ring assembly 76' travels a certain distance upward or downward, membrane assembly 82' may travel the same distance. For example, when magnetic ring assembly 76' travels 2 mm from a position near first electromagnetic coil 77' to a position near second electromagnetic coil 78', membrane assembly 82' may also travel 2 mm in the same direction. Similarly, the frequency at which magnetic ring assembly 76' traverses the space between the first and second electromagnetic coils may be the same frequency at which membrane assembly 82' travels the same distance.

Skirt 115 may be affixed to membrane 97' and hold membrane 97' in tension. Membrane 97' may be molded directly onto skirt 115 or may be affixed to skirt 115 in any way that holds membrane 97' uniformly in tension along its circumference. For example, skirt 115 may be coated with the same material used to form membrane 97' and the coating on skirt 115 may be integrally formed with membrane 97'.

Blood may enter implantable pump 20' from the left ventricle through inlet cannula 21' and flow downward along the pump assembly into delivery channel 100'. As the blood moves down tapered section 83', it is directed through gap 74' and into a vertical portion of delivery channel 100' in the area between pump housing 27' and actuator assembly 95'. As shown in FIG. 15A, skirt 115 divides delivery channel 100' into upper delivery channel 100*a* and lower delivery channel 100*b* such that blood flow through delivery channel 100' is divided into flow channel 101*a* via upper delivery channel 100*a* and flow channel 101*b* via lower delivery channel 100*b*, wherein flow channels 101*a* and 101*b* are separated by membrane 97'. As will be understood by one of ordinary skill in the art, the volume of blood flow through each of delivery channels 100*a* and 100*b* may depend on the diameter of first portion 115*a* of skirt 115. For example, the larger the diameter of first portion 115*a* of skirt 115, the larger the volume of delivery channel 100*a* and the smaller the volume of delivery channel 100*b*. The ratio of the volume of delivery channel 100*a* to the volume of delivery channel 100*b* may be, for example, 1:1, 1:2, 1:3, 1:4, 2:1, 3:1, 4:1, etc., depending on the amount of desired blood flow on each surface of membrane 97'.

Figure 16B:
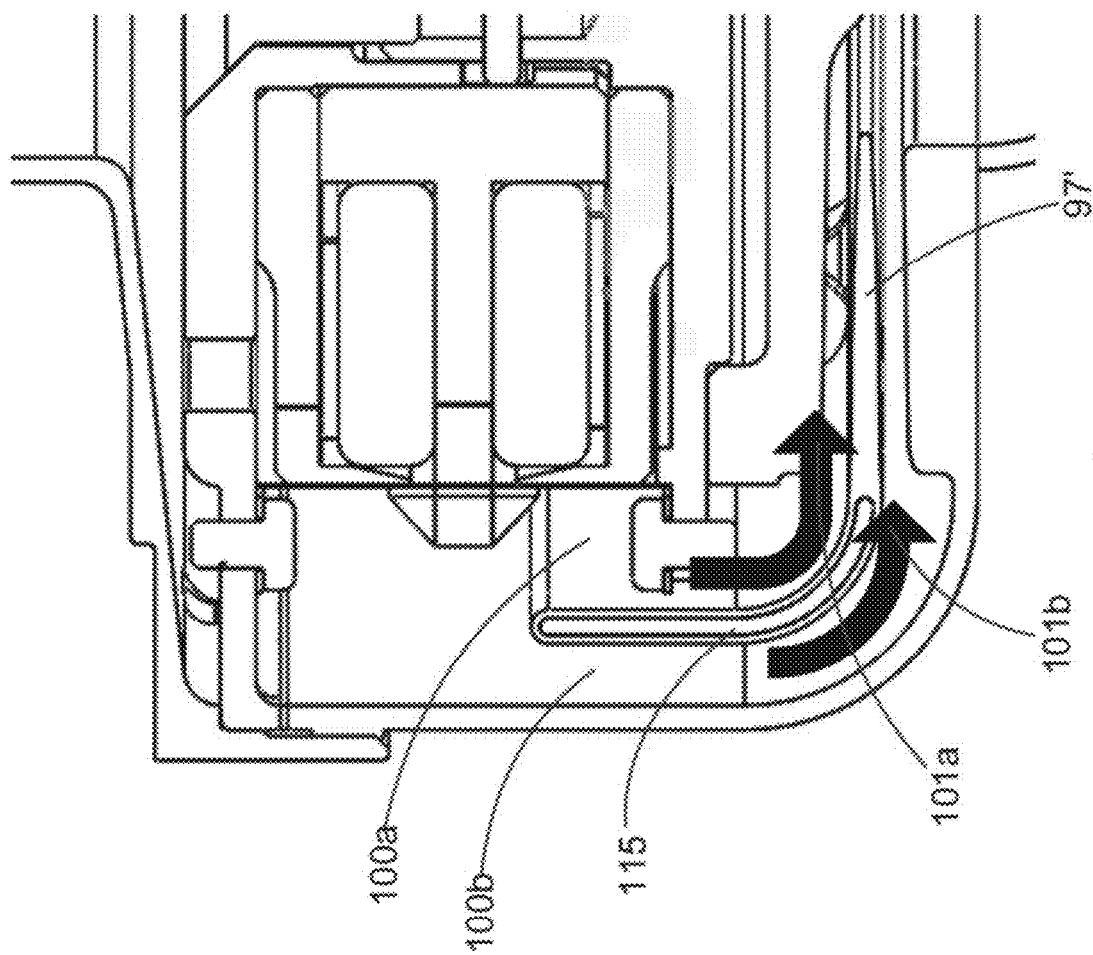
FIG. 16B illustrates blood flow using a pump assembly with a skirt in accordance with one aspect of the present invention.
Figure 16A:
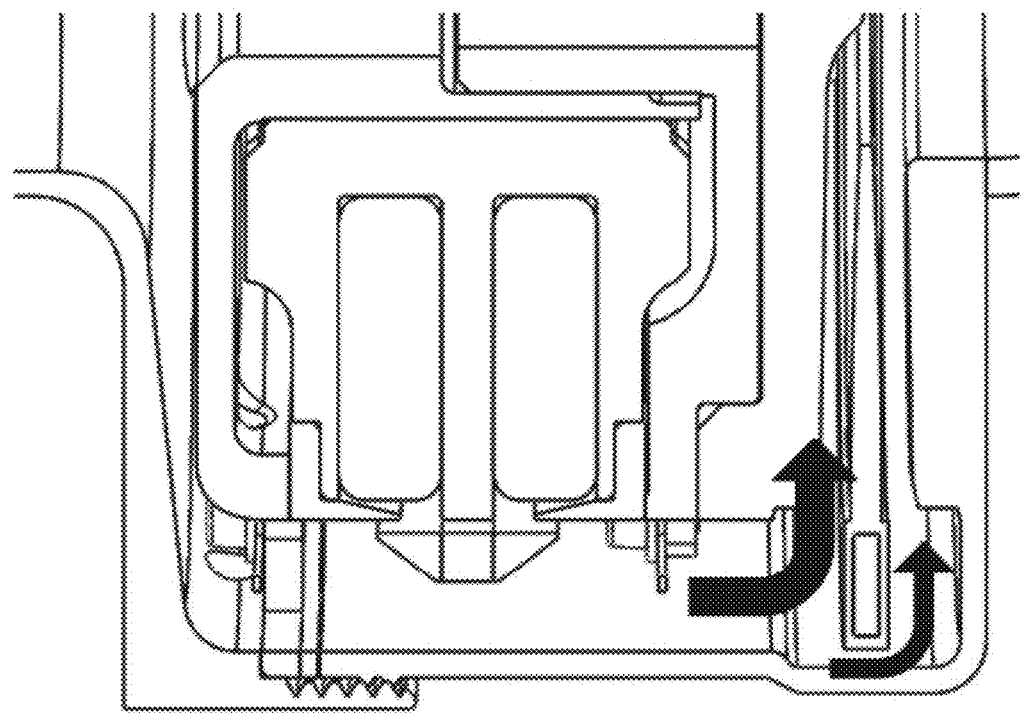

By directing blood from inlet cannula 21' across skirt 115 within delivery channel 100', blood flow is divided into delivery channel 100*a* and 100*b* and to flow channels 101*a* and 101*b*, respectively, such that blood flows across the upper and lower surfaces of membrane 97' of membrane assembly 82'. For example, as shown in FIG. 16A, blood flow through a pump having a planar rigid membrane ring spaced apart a relatively small distance from the pump housing may allow unrestricted blood flow across the upper surface of the flexible membrane while restricting blood flow across the lower surface of the flexible membrane. Whereas, as depicted in FIG. 16B, blood flow through a pump having a J-shaped skirt may be distributed across both the upper and lower sides of the flexible membrane at a desired ratio.

Referring back to FIG. 15A, by actuating electromagnetic coils 77' and 78', membrane 97' may be undulated within flow channels 101*a* and 101*b* to induce wavelike formations in membrane 97' that move from the edge of membrane 97' towards circular aperture 99'. Accordingly, when blood is delivered to membrane assembly 82' from delivery channel 100', it may be propelled radially along both the upper and lower surfaces of membrane 97' towards circular aperture 99', and from there out of outlet 23'. The distribution of blood flow across the upper and lower surfaces of membrane 97' reduces recirculation of blood within delivery channel 101', and reduces repeated exposure of blood to high shear stress areas, which results in remarkably improved hydraulic performance of implantable pump 20'.

Figure 17:
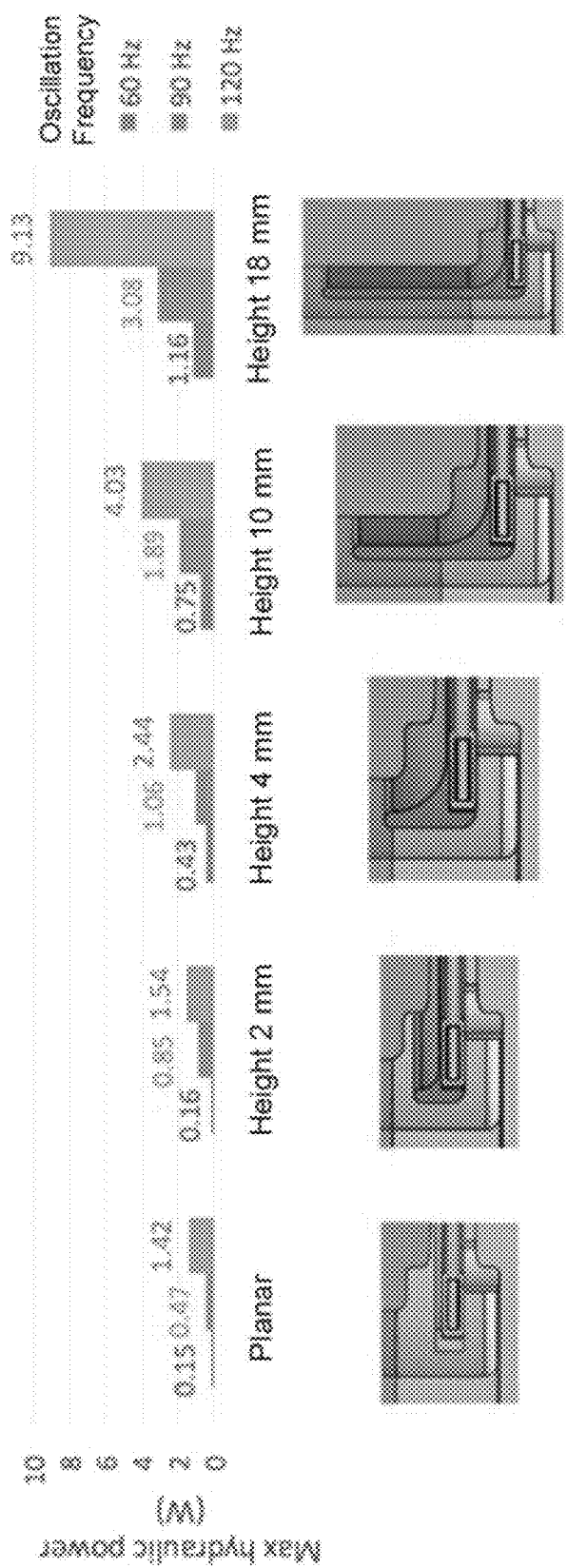
FIG. 17 shows graphs illustrating the relationship between max hydraulic power and the height of the skirt.

Referring now to FIG. 17, the relationship between the maximum hydraulic power of the pump system and the height of the J-shaped skirt is described. As the height of the vertical portion of the skirt increases, the maximum hydraulic power of the pump increases at a non-linear rate. For example, as shown in FIG. 17, operation of a pump having a planar rigid membrane ring at 60 Hz results in a maximum of 0.15 W of hydraulic power, at 90 Hz results in a maximum of 0.47 W of hydraulic power, and at 120 Hz results in a maximum of 1.42 W of hydraulic power. Operation of a pump having a skirt with an extension height of 2 mm, measured from the top surface of the membrane ring to the top of the J-shaped skirt, at 60 Hz results in a maximum of 0.16 W of hydraulic power, at 90 Hz results in a maximum of 0.85 W of hydraulic power, and at 120 Hz results in a maximum of 1.54 W of hydraulic power. Operation of a pump having a skirt with an extension height of 4 mm at 60 Hz results in a maximum of 0.43 W of hydraulic power, at 90 Hz results in a maximum of 1.06 W of hydraulic power, and at 120 Hz results in a maximum of 2.44 W of hydraulic power. Operation of a pump having a skirt with an extension height of 10 mm at 60 Hz results in a maximum of 0.75 W of hydraulic power, at 90 Hz results in a maximum of 1.89 W of hydraulic power, and at 120 Hz results in a maximum of 4.03 W of hydraulic power. Operation of a pump having a skirt with an extension height of 18 mm at 60 Hz results in a maximum of 1.16 W of hydraulic power, at 90 Hz results in a maximum of 3.08 W of hydraulic power, and at 120 Hz results in a maximum of 9.13 W of hydraulic power. As such, height of skirt 115 is preferably at least 2 mm, and more preferably at least 4 mm, at least 10 mm, and/or at least 18 mm. Accordingly, implantable pump 20' may be operated at a significantly lower frequency to achieve the same hydraulic output as a pump having a planar rigid membrane ring operating at a higher frequency, while reducing blood damage and increasing fatigue life of membrane 97' and the springs.

Figure 18:
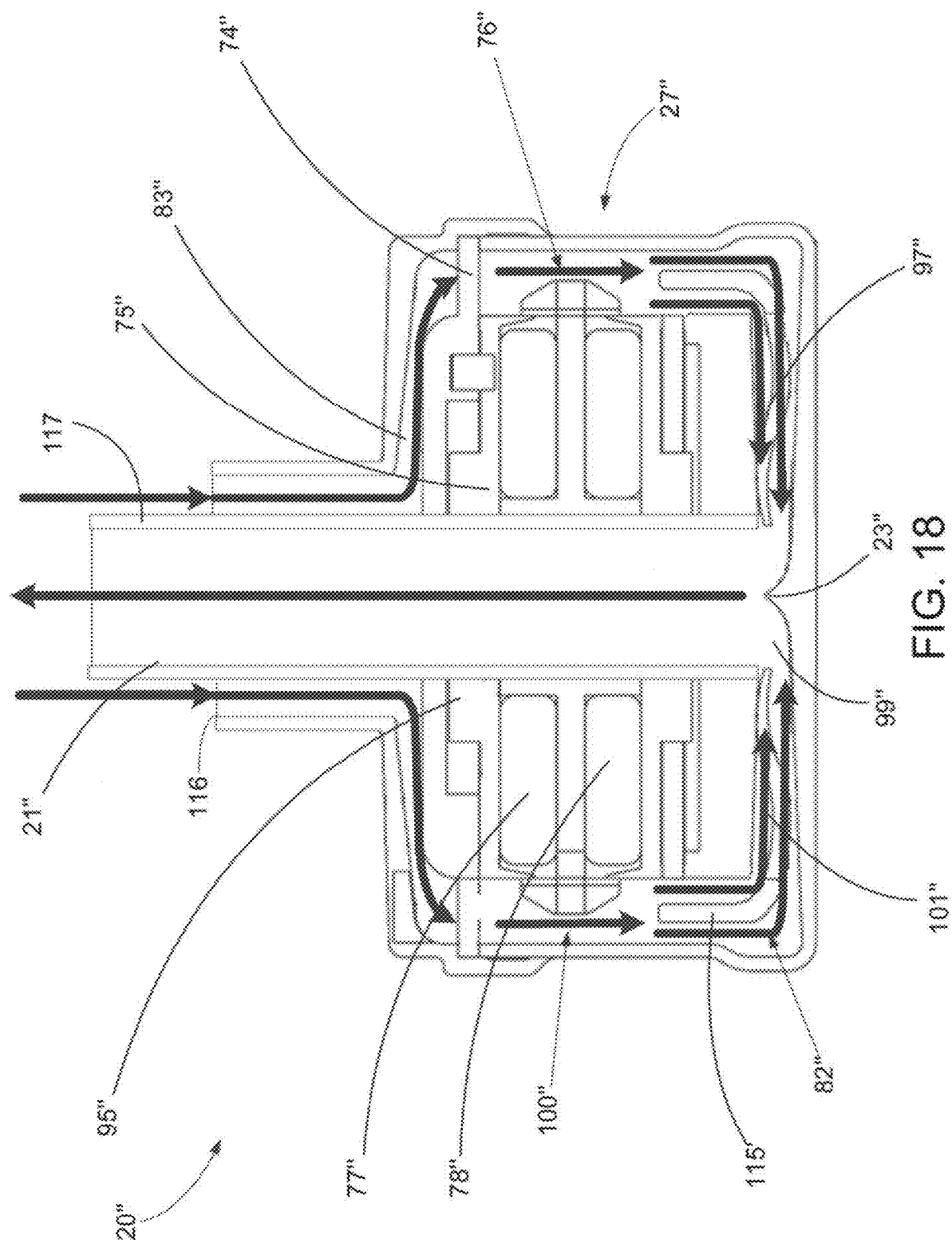
FIG. 18 is a cross-sectional view of yet another alternative exemplary embodiment of an implantable pump of the present invention with improved hydraulic performance, wherein the outflow cannula is disposed coaxially within the inflow cannula.

Referring now to FIG. 18, an alternative exemplary embodiment of the pump assembly of the present invention having a J-shaped skirt is described. Implantable pump 20" is constructed similar to implantable pump 20' described in FIG. 15A, in which similar components are identified with like-double primed numbers. In addition, implantable pump 20" includes skirt 115' which is constructed similar to skirt 115 of FIG. 15A. Implantable pump 20" is distinct from implantable pump 20' in that inlet 21" is coupled to inflow cannula 116, and outlet 23" is coupled to outflow cannula 117 such that outflow cannula 117 is disposed coaxially within inflow cannula 116, as described in U.S. Patent Publication No. 2017/0290967 to Botterbusch, the entire contents of which are incorporated herein by reference. Accordingly, during operation, blood flows into inlet 21" via inflow cannula 116, through delivery channel 100" into flow channel 101" across membrane 97", and exits through outlet cannula 117 via outlet 23".

Figure 19:
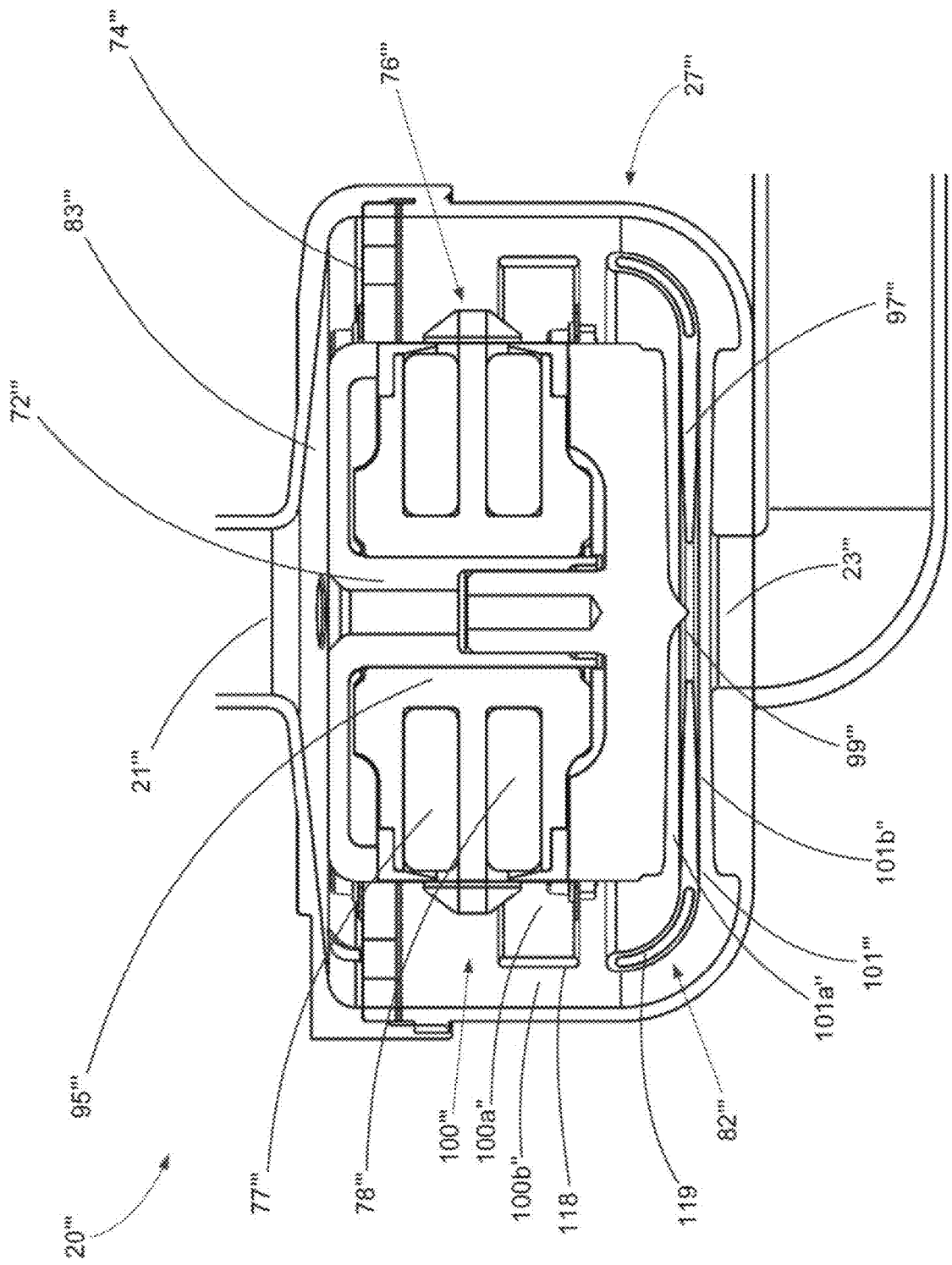
FIG. 19 is a cross-sectional view of yet another alternative exemplary embodiment of an implantable pump of the present invention having a ring and skirt with improved hydraulic performance for use in the pump system of FIG. 1.

Referring now to FIG. 19, another alternative exemplary embodiment of the pump assembly of the present invention is described. Implantable pump 20''' is constructed similar to implantable pump 20' described in FIGS. 15A and 15B, in which similar components are identified with like-double primed numbers and like-triple primed numbers. Implantable pump 20''' is distinct from implantable pump 20' in that implantable pump 20''' includes rigid ring 118 fixed about stator assembly 72'''. Ring 118 extends longitudinally within delivery channel 100''', parallel to the longitudinal axis of stator assembly 72''' such that ring 118 forms a cylindrical-shaped ring about stator assembly 72'''.

In addition, membrane assembly 82''' of implantable pump 20''' includes skirt 119 coupled to membrane 97'''. The upper portion of skirt 119 is substantially parallel to ring 118, and the lower portion of skirt 119 curves toward outlet 23''' such that skirt 119 is coupled to membrane 97'', perpendicular to ring 118. For example, skirt 119 may have a J-shaped cross-section, having a predetermined radius of curvature which allows blood to flow smoothly from delivery channels 100a'' and 100b'' across skirt 119 to the outer edge of membrane 97''' within flow channel 101''', while reducing stagnation of blood flow. Together, ring 118 and skirt 119 breaks flow recirculation of blood within delivery channel 100''' and improves hydraulic power generated for a given frequency while minimizing blood damage. The distance between ring 118 and skirt 119 as skirt 119 reciprocates in response to the magnetic field generated by magnetic ring assembly 76''' as described in further detail below, is minimized to reduce leakage of blood between delivery channels 100a'' and 100b'', and to reduce blood damage. In addition, the J-shape of skirt 119 is significantly more stiff than a planar rigid membrane ring, thereby reducing flexing and fatigue, as well as drag as the blood moves across membrane 97'''.

Skirt 119 is preferably impermeable such that blood cannot flow through skirt 119, and exhibits rigid properties under typical forces experienced during the full range of operation of the present invention and may be made of a biocompatible metal, e.g., titanium. Post reception sites may be formed into skirt 119 to engage membrane assembly 82''' with the posts. Alternatively, the posts may be attached to skirt 119 in any other way which directly translates the motion of magnetic ring assembly 76''' to skirt 119.

As magnetic ring assembly 76''' moves up and down, the movement is rigidly translated by the posts to skirt 119 of membrane assembly 82'''. Given the rigidity of the posts, when magnetic ring assembly 76''' travels a certain distance upward or downward, membrane assembly 82''' may travel the same distance. For example, when magnetic ring assembly 76''' travels 2 mm from a position near first electromagnetic coil 77''' to a position near second electromagnetic coil 78''', membrane assembly 82''' may also travel 2 mm in the same direction. Similarly, the frequency at which magnetic ring assembly 76''' traverses the space between the first and second electromagnetic coils may be the same frequency at which membrane assembly 82''' travels the same distance.

Skirt 119 may be affixed to membrane 97''' and hold membrane 97''' in tension. Membrane 97''' may be molded directly onto skirt 119 or may be affixed to skirt 119 in any way that holds membrane 97''' uniformly in tension along its circumference. For example, skirt 119 may be coated with the same material used to form membrane 97''' and the coating on skirt 119 may be integrally formed with membrane 97'''.

Blood may enter implantable pump 20''' from the left ventricle through inlet 21''' and flow downward along the pump assembly into delivery channel 100'''. As the blood moves down tapered section 83''', it is directed through gap 74''' and into a vertical portion of delivery channel 100''' in the area between pump housing 27''' and actuator assembly 95'''. As shown in FIG. 19, ring 118 divides delivery channel 100''' into upper delivery channel 100a'' and lower delivery channel 100b'' such that blood flow through delivery channel 100''' is divided into flow channel 101a'' via upper delivery channel 100a'' and flow channel 101b'' via lower delivery channel 100b'' and across skirt 119 with minimal leakage between delivery channel 100a'' and delivery channel 100b'', wherein flow channels 101a'' and 101b'' are separated by membrane 97'''.

As will be understood by one of ordinary skill in the art, the volume of blood flow through each of delivery channels 100a'' and 100b'' may depend on the diameter of ring 118 and the curvature of radius of skirt 119. For example, the larger the diameter of ring 118, the larger the volume of delivery channel 100a'' and the smaller the volume of delivery channel 100b''. The ratio of the volume of delivery channel 100a'' to the volume of delivery channel 100b'' may be, for example, 1:1, 1:2, 1:3, 1:4, 2:1, 3:1, 4:1, etc., depending on the amount of desired blood flow on each surface of membrane 97'''. By directing blood from inlet cannula 21'' across ring 118 within delivery channel 100''', blood flow is divided into delivery channels 100a'' and 100b'' and across skirt 119 to flow channels 101a'' and 101b'', respectively, such that blood flows across the upper and lower surfaces of membrane 97''' of membrane assembly 82'''.

By actuating electromagnetic coils 77''' and 78'', membrane 97''' may be undulated within flow channels 101a'' and 101b'' to induce wavelike formations in membrane 97''' that move from the edge of membrane 97''' towards circular aperture 99'''. Accordingly, when blood is delivered to membrane assembly 82''' from delivery channel 100''', it may be propelled radially along both the upper and lower surfaces of membrane 97''' towards circular aperture 99'', and from there out of outlet 23'''. The distribution of blood flow across the upper and lower surfaces of membrane 97''' reduces recirculation of blood within delivery channel 101''', and reduces repeated exposure of blood to high shear stress areas, which results in remarkably improved hydraulic performance of implantable pump 20'''.

Figure 20:
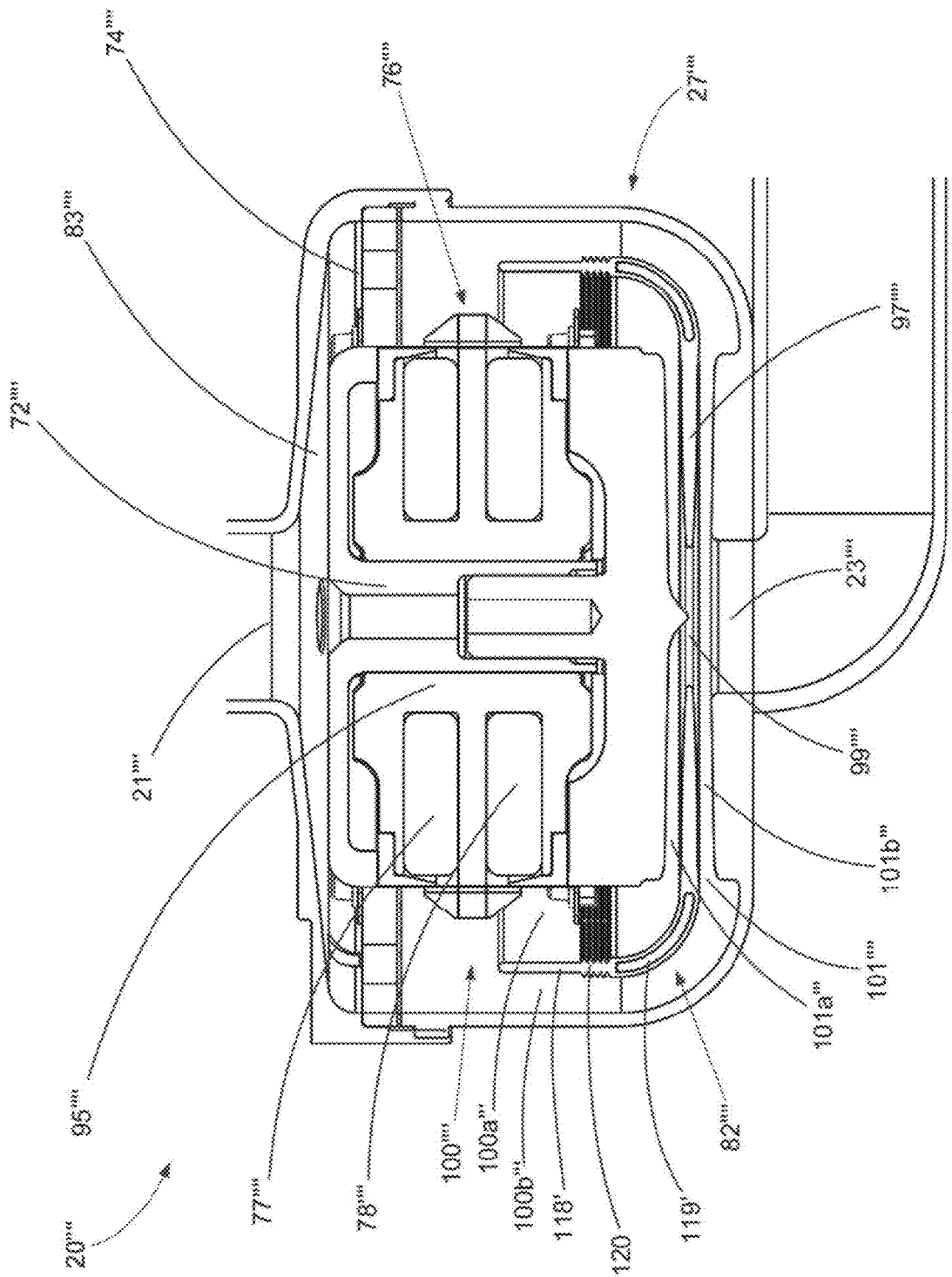
FIG. 20 is a cross-sectional view of yet another alternative exemplary embodiment of an implantable pump of the present invention having a ring, skirt, and expandable portion with improved hydraulic performance for use in the pump system of FIG. 1.

Referring now to FIG. 20, yet another alternative exemplary embodiment of the pump assembly of the present invention is described. Implantable pump 20'''' is constructed similar to implantable pump 20''' described in FIG. 19, in which similar components are identified with like-primed, like-triple primed, and like-quadruple primed numbers. Implantable pump 20'''' is distinct from implantable pump 20''' in that implantable pump 20'''' includes expandable portion 120 coupled between ring 118' and the upper portion of skirt 119'. Expandable portion 120 is impermeable and prevents leakage between delivery channels 100a''' and 100b'''. Preferably, expandable portion 120 has a pleated configuration that may expand and contract to permit efficient reciprocation of skirt 119' relative to ring 118'. For example, expandable portion 120 may comprise a plurality of bellows having a first end coupled to ring 118 ' and a second end coupled to skirt 119'.

Expandable portion 120 may be molded directly onto skirt 119' or may be affixed to skirt 119' in any way that holds expandable portion 120 uniformly along its circumference. Similarly, expandable portion 120 may be molded directly onto ring 118' or may be affixed to ring 118' in any way that holds expandable portion 120 uniformly along its circumference. Skirt 119' may be coated with the same material used to form membrane 97''' and/or expandable portion 120 and the coating on skirt 119' may be integrally formed with membrane 97''' and/or expandable portion 120.

As shown in FIG. 20, expandable portion 120 extends longitudinally within delivery channel 100'''', parallel to the longitudinal axis of stator assembly 72''. Thus, during operation, blood is directed from inlet cannula 21'''' across ring 118' and expandable portion 120 within delivery channel 100'''', and divided into delivery channels 100a''' and 100b''' and across skirt 119' to flow channels 101a''' and 101b''', respectively, such that blood flows across the upper and lower surfaces of membrane 97" of membrane assembly 82".

As magnetic ring assembly 76" moves up and down, the movement is rigidly translated by the posts to skirt 119' of membrane assembly 82", and thereby to expandable portion 120. For example, when magnetic ring assembly 76" travels a certain distance upward or downward, membrane assembly 82" travels the same distance causing expandable portion 120 to expand and contract within delivery channel 100"" parallel to the longitudinal axis of stator assembly 72" by the same distance. Similarly, the frequency at which magnetic ring assembly 76" traverses the space between the first and second electromagnetic coils may be the same frequency at which membrane assembly 82" travels the same distance.

Referring now to FIGS. 21A-21H, various configurations for energizing the implantable pumps of the present invention, e.g., implantable pumps 20, 20", 20"', and 20"", described above are provided. As shown in FIG. 21A, controller 30 includes output port 33 which is electrically coupled to cable 29 as described above, which in turn is coupled to the implantable pump. Controller 30 also includes power connector 103, which may be electrically coupled to a battery, an extension port electrically coupled to a battery, or an AC/DC power supply. For example, power connector 103 may be male, while the connector of the corresponding battery or extension port is female.

In one embodiment, as shown in FIG. 21B, controller 30 includes two power connectors, e.g., first power connector 103 and second power connector 104. As described above, first power connector 103 may be electrically coupled to a first battery, a first extension port electrically coupled to a first battery, or a first AC/DC power supply, and second power connector 103 may be electrically coupled to a second battery, a second extension port electrically coupled to a second battery, or a second AC/DC power supply. In this embodiment, first power connector 103 and second power connector 104 may both be male. In addition, controller 30 includes circuitry for switching between power sources such that energy is selectively transmitted to controller 30 from at least one of the first or second battery/power supply. For example, the circuitry may switch between a first and second battery intermittently, or after the remaining power level of one of the batteries reaches a predetermined threshold.

Referring now to FIGS. 21C-E, configurations are illustrated wherein controller 30 is directly electrically coupled to battery 40, such that controller 30 and battery 40 may be worn by the patient together, e.g., via a purse, shoulder bag, or holster. As shown in FIG. 21C, controller 30 of FIG. 21A may be electrically coupled to battery 40 via power connector 103, wherein power connector 103 is male and battery 40 has a corresponding female connector. For example, FIG. 21D illustrates controller 30 electrically coupled to battery 40, wherein battery 40 has a smaller size, and therefore lower capacity, and FIG. 21E illustrates controller 30 electrically coupled to battery 40, wherein battery 40 has a larger size, and therefore higher capacity. As will be understood by a person of ordinary skill in the art, battery 40 may have various sizes depending on the need of the patient.

Referring now to FIGS. 21F-H, configurations are illustrated wherein controller 30 is remotely electrically coupled to battery 40, such that the weight and volume of controller 30 and battery 40 are distributed and may be worn by the patient separately, e.g., via a belt or a vest. As shown in FIG. 21F, cable 41, which electrically couples controller 30 to battery 40, is electrically coupled to first power connector port 105 via strain relief 106, which is a hardwired junction between cable 41 and first power connector port 105. Power connector port 105 includes power connector 107, which may be electrically coupled to a battery. For example, power connector 107 may be male, while the connector of the corresponding battery is female.

As shown in FIG. 21G, controller 30 may be remotely electrically coupled to battery 40 via cable 41. Cable 41 is electrically coupled at one end to controller 30 via second power connector port 108 and strain relief 114, which is a hardwired junction between cable 41 and second power connector port 108, and electrically coupled at another end to battery 40 via first connector port 105 and strain relief 106. For example, power connector 103 of controller 30 may be male while the connector of corresponding second power connector port 108 is female, and power connector 107 of first power connector port 105 may be male while the connector of corresponding battery 40 is female.

In one embodiment, as shown in FIG. 21H, controller 30 may be remotely electrically coupled to multiple batteries, e.g., battery 40A and battery 40B, via a single second power connector port 108. As shown in FIG. 21H, second power connector port 108 includes first strain relief 114A and second strain relief 114B, such that controller 30 is remotely electrically coupled to battery 40A via cable 41A and remotely electrically coupled to battery 40B via cable 41B. Specifically, cable 41A is electrically coupled at one end to controller 30 via second power connector port 108 and first strain relief 114A, and electrically coupled at another end to battery 40A via first connector port 105A and strain relief 106A, and cable 41B is electrically coupled at one end to controller 30 via second power connector port 108 and second strain relief 114B, and electrically coupled at another end to battery 40B via first connector port 105B and strain relief 106B. In this embodiment, controller 30 may include circuitry for switching between battery 40A and battery 40B such that energy is selectively transmitted to controller 30 from at least one of battery 40A and battery 40B. For example, the circuitry may switch between battery 40A and battery 40B intermittently, or after the remaining power level of one of the batteries reaches a predetermined threshold. Alternatively, controller 30 may receive energy from battery 40A and battery 40B simultaneously.

In another embodiment, as shown in FIG. 21I, controller 30 is electrically coupled to AC/DC power supply 109, which may be plugged into an electrical outlet via AC plug 113, e.g., when the patient is resting bedside. Specifically, AC/DC power supply 109 is electrically coupled to controller 30 via cable 41, such that cable 41 is electrically coupled at one end to controller 30 via second power connector port 108 and strain relief 114, and electrically coupled at another end to AC/DC power supply 109 via first power supply port 110. In addition, AC/DC power supply 109 is electrically coupled to plug 113 via cable 112 and second power supply port 111.

Controller 30 may include an internal battery, such that the internal battery powers controller 30 and the implantable pump during the time required for battery 40 to be replaced and/or recharged. Accordingly, controller 30 may include circuitry for switching between power sources such that energy is transmitted to controller 30 from the internal battery while battery 40 is disconnected from controller 30, and from battery 40 when battery 40 is electrically coupled to controller 30. In addition, the circuitry may allow battery 40 to charge the internal battery while also energizing the implantable pump until the internal battery is recharged to a desired amount, at which point the circuitry allows battery 40 to solely energize the implantable pump. Similarly, when controller 40 is electrically coupled to AC/DC power supply 109, the circuitry may allow AC/DC power supply 109 to charge the internal battery while also energizing the implantable pump until the internal battery is recharged to a desired amount, at which point the circuitry allows AC/DC power supply 109 to solely energize the implantable pump.

While various illustrative embodiments of the invention are described above, it will be apparent to one skilled in the art that various changes and modifications may be made therein without departing from the invention. For example, pump assembly 70 shown in FIG. 9 may be ordered differently and may include additional or fewer components of various sizes and composition. The appended claims are intended to cover all such changes and modifications that fall within the true spirit and scope of the invention.

What is claimed is:

1. An implantable blood pump system comprising:
a housing having an inlet and an outlet and configured to be implanted at a patient's heart;
a membrane disposed within the housing;
an actuator disposed within the housing; and
a skirt disposed within the housing to at least partially surround the actuator and define a delivery channel between the housing and the skirt, the skirt sized and shaped to extend toward the inlet and to curve toward the outlet,
wherein the actuator is configured to cause the membrane to reciprocate and deform in a wave-like manner during operation such that blood enters the inlet, flows in the delivery channel, is guided by the skirt toward the membrane, and is propelled across the membrane to the outlet.

2. The implantable blood pump system of claim 1, wherein a first portion of the skirt encircles at least a portion of the actuator.

3. The implantable blood pump system of claim 2, wherein the first portion extends towards the inlet.

4. The implantable blood pump system of claim 2, wherein a second portion of the skirt comprises a radius of curvature that extends from the first portion towards the outlet.

5. The implantable blood pump of system of claim 4, wherein the membrane is coupled to the second portion of the skirt.

6. The implantable blood pump system of claim 1, wherein the skirt is coupled to the membrane and the delivery channel is configured to direct blood from the inlet to the membrane.

7. The implantable blood pump system of claim 1, wherein at least a portion of the skirt is J-shaped and configured to resist fatigue.

8. The implantable blood pump system of claim 1, wherein the actuator comprises a stationary portion comprising at least one electromagnetic coil and a moving portion comprising at least one magnet configured to be engaged by the at least one electromagnetic coil.

9. The implantable blood pump system of claim 8, wherein the skirt is coupled to the moving portion of the actuator.

10. The implantable blood pump system of claim 1, wherein the membrane comprises a central aperture.

11. The implantable blood pump system of claim 1, wherein the skirt is formed from impermeable material such that blood cannot flow through the skirt.

12. The implantable blood pump system of claim 1, further comprising a flow channel within the housing and perpendicular to the delivery channel,
wherein the skirt is configured to guide the blood from the delivery channel into the flow channel toward the membrane.

13. An implantable blood pump system comprising:
a housing having an inlet and an outlet and configured be to in fluid communication with a patient's heart;
an actuator disposed within the housing and comprising a stationary portion coupled to the housing and a moving portion;
a membrane assembly disposed within the housing and coupled to the moving portion of the actuator, the membrane assembly encircling at least a portion of the stationary portion of the actuator and comprising a membrane; and
wherein the actuator is configured to cause the membrane to move in a wave-like manner to cause blood to enter the inlet and be propelled across the membrane to the outlet.

14. The implantable blood pump system of claim 13, wherein the membrane assembly and the housing define a delivery channel between the inlet and the outlet.

15. The implantable blood pump system of claim 14, wherein the delivery channel is configured to direct blood towards the membrane.

16. The implantable blood pump system of claim 15, further comprising a flow channel within the housing and perpendicular to the delivery channel,
wherein the membrane assembly is configured to guide the blood from the delivery channel into the flow channel toward the membrane.

17. The implantable blood pump system of claim 13, wherein the membrane assembly is sized and shaped to extend towards the inlet and to curve towards the outlet.

18. The implantable blood pump system of claim 17, wherein a first portion of the membrane assembly surrounds at least a portion of the actuator and extends toward the inlet.

19. The implantable blood pump system of claim 18, wherein the first portion of the membrane assembly is coupled to the moving portion of the actuator.

20. The implantable blood pump system of claim 18, wherein a second portion of the membrane assembly comprises a radius of curvature that extends from the first portion towards the outlet and is coupled to the membrane.

21. The implantable blood pump system of claim 13, wherein the stationary portion of the actuator comprises at least one electromagnetic coil and the moving portion of the actuator comprises at least one magnet configured to be engaged by the at least one electromagnetic coil.

22. The implantable blood pump system of claim 13, wherein the membrane assembly comprises a first portion and a second portion separated from the first portion.

23. The implantable blood pump system of claim 13, wherein the membrane comprises a central aperture.

24. The implantable blood pump system of claim 13, wherein at least a portion of the membrane assembly is formed from impermeable material such that blood cannot flow through the impermeable material.

* * * * *